United States Patent
Hirabayashi et al.

(10) Patent No.: US 8,008,094 B2
(45) Date of Patent: Aug. 30, 2011

(54) METHODS FOR ANALYZING INTERACTIONS BETWEEN PROTEINS AND SUGAR CHAINS

(75) Inventors: Jun Hirabayashi, Tsukuba (JP); Atsushi Kuno, Tsukuba (JP); Sachiko Nakamura, Tsukuba (JP); Noboru Uchiyama, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 760 days.

(21) Appl. No.: 10/596,692

(22) PCT Filed: Dec. 24, 2004

(86) PCT No.: PCT/JP2004/019333
§ 371 (c)(1),
(2), (4) Date: Sep. 21, 2006

(87) PCT Pub. No.: WO2005/064333
PCT Pub. Date: Jul. 14, 2005

(65) Prior Publication Data
US 2007/0202535 A1 Aug. 30, 2007

(30) Foreign Application Priority Data
Dec. 25, 2003 (JP) .................................. 2003-430848

(51) Int. Cl.
*G01N 33/53* (2006.01)

(52) U.S. Cl. ....... 436/518; 435/7.1; 435/7.92; 435/7.94; 435/7.95; 435/283.1; 435/288.3; 435/288.7; 435/970; 436/527

(58) Field of Classification Search .................. 435/7.1, 435/7.92, 7.94, 7.95
See application file for complete search history.

(56) References Cited

U.S. PATENT DOCUMENTS

| | | |
|---|---|---|
| 5,500,342 A | 3/1996 | Miyamura et al. |
| 6,054,047 A | 4/2000 | Hindsgaul et al. |
| 6,395,169 B1 | 5/2002 | Hindsgaul et al. |
| 6,630,356 B1 | 10/2003 | Armstrong et al. |
| 6,707,561 B1 | 3/2004 | Budach et al. |
| 7,056,678 B1 | 6/2006 | Markman et al. |
| 7,132,251 B1 | 11/2006 | Markman |

(Continued)

FOREIGN PATENT DOCUMENTS

AU 2004-210601 A1 10/2004

(Continued)

OTHER PUBLICATIONS

U.S. Appl. No. 10/596,704, Hirabayashi et al.
D. Guschin et al. "Manual Manufacturing of Oligonucleotide, DNA, and Protein Microchips" Analytical Biochemistry 250, pp. 203-211 (1997).
A. Lueking et al."Protein Microarrays for Gene Expression and Antibody Screening", Analytical Biochemistry 270, pp. 103-111 (1999).

(Continued)

*Primary Examiner* — Bao Thuy L Nguyen
(74) *Attorney, Agent, or Firm* — Klarquist Sparkman, LLP

(57) ABSTRACT

As a result of investigating the optimum conditions of methods for immobilizing proteins that interact with sugar chains onto a substrate, it was revealed that coating the surface of a slide glass with GTMS enables immobilization at a higher S/N ratio than conventionally possible. Moreover, by using a substrate to which a rubber with a number of holes was affixed to form a number of reaction vessels, and further by spotting lectins onto the substrate and washing with PBST, the weak interactions between sugar chains and lectins were successfully detected with improved sensitivity. In addition, by introducing an evanescent excitation-type scanner, it became possible to detect the interactions between lectins and sugar chains without washing away the probe solution.

13 Claims, 14 Drawing Sheets

U.S. PATENT DOCUMENTS

| | | | |
|---|---|---|---|
| 2002/0074513 A1 | 6/2002 | Abel et al. | |
| 2002/0192680 A1* | 12/2002 | Chan et al. | 435/6 |
| 2003/0232382 A1* | 12/2003 | Brennan et al. | 435/6 |
| 2004/0067539 A1 | 4/2004 | Carlsson et al. | |
| 2004/0146920 A1* | 7/2004 | Lee et al. | 435/6 |
| 2004/0203040 A1 | 10/2004 | Okada | |
| 2004/0248144 A1* | 12/2004 | Mir | 435/6 |
| 2006/0194269 A1 | 8/2006 | Markman | |
| 2007/0092915 A1 | 4/2007 | Markman et al. | |
| 2007/0167608 A1 | 7/2007 | Hirabayashi et al. | |
| 2007/0202535 A1 | 8/2007 | Hirabayashi et al. | |
| 2009/0041630 A1 | 2/2009 | Hirabayashi et al. | |

FOREIGN PATENT DOCUMENTS

| | | |
|---|---|---|
| EP | 1211514 | 6/2002 |
| EP | 1 445 330 A1 | 8/2004 |
| JP | 8-201382 | 8/1996 |
| JP | 8-201383 A | 8/1996 |
| JP | 2001-520104 | 10/2001 |
| JP | 2001-311690 | 11/2001 |
| JP | 2002-544485 | 12/2002 |
| JP | 2003-503732 A | 1/2003 |
| JP | 2003-035710 | 2/2003 |
| JP | 2003-508729 A | 3/2003 |
| JP | 2003-116554 | 4/2003 |
| JP | 2003-527605 A | 9/2003 |
| JP | 2004-258026 A | 9/2004 |
| JP | 2002-107366 | 4/2010 |
| WO | 96/35940 | 11/1996 |
| WO | WO-99/19892 A1 | 4/1999 |
| WO | WO-00/68688 A1 | 11/2000 |
| WO | WO 01/16600 | 3/2001 |
| WO | 02/44412 A1 | 6/2002 |
| WO | WO 02/083918 | 10/2002 |
| WO | WO-02/092615 A2 | 11/2002 |

OTHER PUBLICATIONS

L Holt, etal., "By-passing Selection: Direct Screening for Antibody—Antigen Interactions Using Protein Arrays", Nucleic Acids Research, 2000, vol. 28, No. 15.
P. Mitchell "A Perspective on Protein Microarrays", Nature Biotechnology, Mar. 2002, vol. 20, pp. 225-229.
H. Zhu, et al. "Analysis of Yeast Protein Kinases Using Protein Chips", Nature Genetics, vol. 26, Nov. 2000, pp. 283-289.
H. Zhu, et al., "Global Analysis of Protein Activities Using Proteome Chips" Science, vol. 293, Sep. 14, 2001, pp. 2101-2105.
International Search Report for PCT/JP2004/019333 mailed Feb. 8, 2005.
International Preliminary Report of Patentability for PCT/JP2004/019333 issued Aug. 22, 2006.
Rosenfeld, et al. U-c Fingerprint: Glycoprotein Analysis Based on a Lectin Array, Glycobiology, vol. 13, No. 11, Nov. 2003. (XP008049528).
Uchiyama, et al., Development of Lectin-microarrays to Profile Glycoprotein Glycosylation under Equilibrium conditions with tan Evanescent Field Fluorescenceå@detection Principle, Glycobiology, vol. 14, No. 11, Nov. 2004. (XP009088873).
Kuno, et al., Evanescent-field fluorescence-assisted lectin microarray: a new strategy for glycan profiling , Nature Methods, vol. 2, No. 11, Nov. 2005. (XP009088872).
J. Hirabayashi, Glycome analysis techniques which use lectin affinity, Tanpakushitsu Kakusan Koso, Aug. 2003, vol. 48, No. 11, pp. 1534-1542.
Arata et al., "Application of Reinforced Frontal Affinity Chromatography and Advanced Processing Procedure to the Study of the Binding Property of a Caenorhabditis elegans Galectin," Journal of Chromatography, vol. 905, pp. 337-343, 2001.
Arata et al., "Sugar binding Properties of the Two Lectin Domains of the Tandem Repeat-type Galectin LEC-1 (N32) of Caenorhabditis elegans," Journal of Biological Chemistry, vol. 276, No. 5, pp. 3068-3077, 2001.
Array Pro Analyzer (v 4.5) product description.
Blixt et al., "Printed covalent glycan array for ligand profiling of diverse glycan binding proteins," PNAS, vol. 101, No. 49, pp. 17033-17038, 2004.
Chan et al., "Frontal affinity chromatography for the screening of mixtures," Combinatorial Chemistry & High Throughput Screening, vol. 5, No. 5, pp. 395-406, 2002.
Hirabayashi, "Oligosaccharide microarrays for glycomics," Trends in Biotechnology, vol. 21, No. 4, pp. 141-143, 2003.
Hirabayashi, "Structural Glycomics and Glycan Profiling," Dai 24 Kai Japanese Society of Carbohydrate Research Yoshishu, The Japanese Society of Carbohydrate Research, pp. 7, 2003.
Hirabayashi, "Perspective: Functional Glycomics," Dai 53 Kai Japanese Electrophoresis Society Symposium Post Genome Kenkyu no, pp. 4-6, 2003.
Hirabayashi et al., "Frontal Affinity Chromatography," Tanpakushitsu Kakusan Koso (Protein, Nucleic Acid and Enzyme), vol. 48, No. 8 suppl., pp. 1206-1212, 2003.
Hirabayashi, "Glycoproteomics and Sugar Chain Profiling Using Lectins," Proceeding of the Biotechnology Symposium, vol. 21, pp. 10-11, 2003.
Hirabayashi et al., "Oligosaccharide Specificity of Galectins: A Search by Frontal Affinity Chromatography," Biochimica et Biophysica Acta, vol. 1572, No. 2-3, pp. 232-254, 2002.
Hirabayashi et al., "Reinforcement of Frontal Affinity Chromatography for Effective Analysis of Lectin-Oligosaccharide Interactions," Journal of Chromatography, vol. 890, No. 2, pp. 261-271, 2000.
Hirabayashi, "Seimeisa o Rikai suru—Tosa Kenkyu no Genjo," Nikkei Science, vol. 33, No. 11, p. 116, 2003.
Joos et al., "Miniaturised multiplexed immunoassays," Current Opinion in Chemical Biology, vol. 6, pp. 76-80, 2001.
Kuno et al., "Evanescent-field fluorescence-assisted lectin microarray: a new strategy for glycan profiling," Nature Methods, vol. 2, No. 11, pp. 851-856, 2005.
Nakamura et al., "Comprehensive Interaction Analysis Between Plant Lectins and PA-oligo Saccharides by an Automated FAC System," Seikagaku, vol. 75, No. 8, p. 1047 (#4P-068), 2003.
Nilsson, "Lectins: proteins that interpret the sugar code," Analytical Chemistry, vol. 75, No. 15, pp. 348-353, 2003.
Nippon Kogyo Shinbun, 2003, p. 20.
Okazaki, "Biacore Applications for Glycoconjugate Research," Trends in Glycoscience and Glycotechnology, vol. 10, No. 54, pp. 321-329, 1998.
Pawlak et al., "Zeptosens' protein microarrays: a novel high performance microarray platform for low abundance protein analysis," Proteomics, vol. 2, pp. 383-393, 2002.
Shalon et al., "A DNA microarray system for analyzing complex DNA samples using two-color fluorescent probe hybridization," Genome Res., vol. 6, pp. 639-645, 1996.
Uchiyama et al., "Optimization of evanescent-field fluorescence-assisted lectin microarray for high-sensitivity detection of monovalent oligosaccharides and glycoproteins," Proteomics, vol. 8, No. 15, pp. 3042-3050, 2008.
Zeng et al., "Analysis of specific interaction of synthetic glycopolypeptides carrying N-acetyllactosamine and related compounds with lectins," Carbohydrate Research, vol. 312, pp. 209-217, 1998 (Abstract Only).
International Search Report dated Oct. 19, 2004 issued for International Application No. PCT/JP2004/009600.
International Preliminary Report on Patentability dated Jul. 27, 2006 issued for International Application No. PCT/JP2004/009600.
Non-Final Office action issued Aug. 18, 2009, for U.S. Appl. No. 10/596,704.
Final Office action issued Feb. 3, 2010, for U.S. Appl. No. 10/596,704.
Non-Final Office action issued May 11, 2010, for U.S. Appl. No. 10/596,704.
Non-Final Office action issued Apr. 26, 2010, for U.S. Appl. No. 11/917,921.

* cited by examiner

METHODS FOR ANALYZING INTERACTIONS BETWEEN PROTEINS AND SUGAR CHAINS

CROSS REFERENCE TO PRIOR RELATED APPLICATIONS

This application is a U.S. national phase application under 35 U.S.C. §371 of International Patent Application No. PCT/JP2004/019333, filed Dec. 24, 2004, and claims the benefit of Japanese Patent Application No. 2003-430848, filed Dec. 25, 2003, both of which are incorporated by reference herein. The International Application was published in Japanese on Jul. 14, 2005 as International Publication No. WO 2005/064333 A1 under PCT Article 21(2).

TECHNICAL FIELD

The present invention relates to methods for analyzing interactions between proteins and sugar chains.

BACKGROUND ART

Proteins are major players carrying out vital functions in the body, and in order to systematically exert their functions in the cellular society, post-translational modifications such as sugar chain modifications play a very important role. Nearly all proteins in the body undergo sugar chain modifications. Recently, there has been a string of reports revealing that sugar chains added to proteins play important roles in various life phenomena such as viral infections, protozoan parasitism and infections, toxin binding, hormone binding, fertilization, development and differentiation, protein stability, cancer cell metastasis and apoptosis.

To analyze the function of a sugar chain, it is first essential to analyze the sugar chain's structure. The importance of methods for analyzing sugar chain structure is predicted to increase in the future. However, since analyses of sugar chain structures require considerable time, labor, and experience, instead of aiming to completely determine structures based on conventional techniques, the development of systems capable of extracting the characteristics of a diversity of sugar chain structures, and mutually distinguishing these structures with greater ease, speed, sensitivity and accuracy, has been expected.

Microarray is a generic term for an apparatus onto which various types of immobilized samples, such as DNAs and proteins, are immobilized on a solid phase carrier (glass, membrane, or silicon chip) in the form of high density spots; microarrays can detect the presence or absence of molecules (hereinafter referred to as probes) that specifically bind to the various sample spots immobilized onto the carrier. The probe molecules used are typically fluorescently labeled, and after reacting a probe solution with an array surface, probe molecules that have bound to each sample spot can be quantitatively analyzed by observation using a fluorescence detection scanner. Since the development of a DNA microarray by Affimetrix Corp. in the U.S., microarrays have been used in an extremely wide range of research fields and have brought various new findings to the human race.

If, when studying the structural and functional information of sugar chains, which are called the third life chain, it were possible to use a microarray for the rapid and highly sensitive large-scale analysis of the interactions between sugar chains and the proteins that interact with sugar chains (sugar-binding proteins, for example lectins, etc), then this could conceivably become an extremely useful tool, applicable over a wide range of applications, from basic research to medical diagnoses and industrial applications.

Compared to the typical dissociation constants and such of antigen-antibody reactions ($K_d=10^{-8}$ or less), the binding between sugar chains and proteins that interact with sugar chains is known to generally be a weak interaction, with dissociation constants ($K_d$) frequently $10^{-6}$ M or more. In addition, the interactions between sugar chains and proteins that interact with sugar chains are known to consist of relatively rapid dissociation-association reactions. As a result, the equilibrium tends to shift towards dissociation due to washing procedures and such, as compared to typical protein-protein interactions or interactions between complementary nucleotide fragments. For example, when purifying lectins with a glycoprotein-immobilized column and such, the lectins are frequently observed to run off the column during the washing procedure, when their binding is weak.

In typical microarray technology using a conventional slide glass, a probe solution is contacted with an immobilized sample and a binding reaction takes place, then the probe solution is washed away, and moisture adhering to the slide glass is completely removed using a jet of gas or a centrifuge, followed by imaging using a microarray scanner. This is because a typical microarray reader cannot examine fluorescence on a slide glass on which there is moisture adhered. Since the dissociation rate constant is sufficiently small for strong binding interactions, such as those between complementary nucleotide fragments and antigen-antibody reactions, the dissociation reaction of probe molecules is not thought to proceed easily, even when the probe solution is removed at a stage prior to scanning. However, when examining interactions with a large dissociation constant, i.e. the weak interactions generally seen between sugar chains and proteins that interact with sugar chains, a dissociation reaction proceeds between these sugar chains and proteins upon removal of the probe solution and the washing procedure, making it difficult to obtain accurate data on interactions under conditions of equilibrium. Consequently, this procedure of washing the probe solution presents a significant problem when accurately analyzing data on the interactions between sugar chains and proteins that interact with sugar chains under conditions of equilibrium in a microarray.

DNA microarrays are currently in a wide range of use. Future application of protein microarrays is expected in basic research fields involving the elucidation and such of the functions of proteins, which are the transcription products of DNA, in the body, and in application fields involving diagnoses, evaluation, and such based on quantitative and qualitative protein changes. Active studies are also being conducted throughout the world in the field of research. However, the development and popularization of protein microarrays is currently far behind that of DNA microarrays. One of the reasons for this, as pointed out early on by numerous researchers, is that it is technically very difficult to immobilize protein samples with various differing properties at a constant rate, while maintaining their activity.

Examples of methods for immobilizing proteins on an array comprise a method developed very early on, in which proteins are physically adsorbed onto a membrane, as exemplified by PVDF membranes (Non-Patent Document 1). Although there are reports that activity is maintained to a certain extent for some proteins such as transcription factors, this is generally not the case. In addition, array density was limited when immobilizing proteins onto a membrane. Although research has progressed towards the immobilization of proteins onto solid surfaces such as metal and glass to achieve higher densities, proteins are generally easily denatured by contact with a solid surface such as metal or glass. Consequently, dedicated research and development have been conducted on immobilization methods that use some linker to crosslink the solid surfaces and proteins.

An example of a method for reducing the problem of protein denaturation involves a method in which a polyacrylamide pad 10 μm to 100 μm thick is attached onto a slide glass, followed by the spotting of proteins (Non-Patent Documents 2 and 3). In this case, since the proteins are immobilized in a three-dimensional space, a quantitative improvement of 100 times or more can be expected compared to methods of immobilization onto a two-dimensional surface. In addition, there is also a method in which proteins are immobilized in a porous polyacrylamide gel via their amino groups (Non-Patent Document 4). However, these methods have not been popularized since they are costly and require the production of special slide glasses. In addition, depending on the detection method, a thick layer of immobilized proteins may not be preferable.

One method for immobilizing proteins onto a solid phase, which is now being most actively investigated, is a method by which proteins are expressed with some tag attached thereto, and this tag is used to immobilize the protein onto a solid carrier. This method is said to improve the effective ligand concentration of the proteins, and to theoretically allow alignment of protein orientation. Examples of such methods comprise a method for using oligohistidine tags to immobilize proteins onto a substrate whose surface is modified with a nickel complex (Non-Patent Document 5), and a method for immobilizing via avidin-biotin (Patent Document 1).

These methods are considered to be effective in terms of immobilizing proteins while retaining their activity or enabling a uniform immobilization rate. However, it is expensive and labor-intensive to add a tag at the genetic level to all proteins for which immobilization onto a microarray is being attempted, and to then express these proteins in *Escherichia coli*, a cell-free system or such, and purify them. Thus, at the present time, these methods are difficult for ordinary researchers to use easily and in a form that flexibly responds to individual needs.

In contrast, methods that utilize protein functional groups to immobilize proteins onto a solid phase carrier can characteristically immobilize proteins extracted from nature as is, or commercially available protein samples as is, for use in microarrays. Examples of methods for immobilizing proteins onto a solid phase carrier via protein amino groups comprise methods in which proteins are immobilized via active ester groups bound to the solid phase surface, and methods in which proteins are immobilized via epoxy groups arranged on the solid phase surface (Non-Patent Document 6). Methods for immobilizing proteins via their amino groups are simple, however, they also enable easy immobilization of commercially available proteins, biological extracts and components, recombinant proteins without specific tags, and such. Therefore, individual users are able to freely select a protein that suits their purpose, and to rapidly and inexpensively optimize this protein for use in a microarray that suits the purpose. Examples of disadvantages in the methods in which proteins are immobilized via amino groups include the fact that the number of lysine residues in a protein differs for each protein, and there is a possibility of inactivating the protein depending on the location of the lysine group used for immobilization.

[Patent Document 1] Japanese Patent Application No. 2001-520104

[Patent Document 2] Japanese Patent Application Kokai Publication No. (JP-A) H08-201383 (unexamined, published Japanese patent application)

[Patent Document 3] Japanese Patent Kohyo Publication No. (JP-A) 2002-544485 (unexamined Japanese national phase publication corresponding to a non-Japanese international publication)

[Non-Patent Document 1] L. J. Holt, K. Bussow, G. Walter, I. M. Tomlinson, Nucleic Acids Res., 15, E72, 2000

[Non-Patent Document 2] D. Guschin, G Yershov, A. Zaslaysky, A. Gemmell, V. Shick, D. Proudnikov, P. Arenkov, A. Mirzabekov, Anal. Biochem., 250, 203-211, 1997

[Non-Patent Document 3] A. Lueking, M. Horn, H. Eickhoff, K. Bussow, H. Lehrach, G Walter, Anal. Biochem., 270, 103-111, 1999

[Non-Patent Document 4] P. Mitchell, Nat. Biotechnol., 20, 225-229, 2002

[Non-Patent Document 5] H. Zhu, M. Bilgin, R. Bangham, D. Hall, A. Casamayor, P. Bertone, N. Lan, R. Jansen, S. Bidlingmaier, T. Houfek, T. Mitchell, P. Miller, R. A. Dean, M. Gerstein, M. Snyder, Science, 293, 2101-2105, 2001

[Non-Patent Document 6] H. Zhu, J. F. Klemic, S. Chang, P. Bertone, A. Casamayor, K. G. Klemic, D. Smith, M. Gerstein, M. A. Reed, M. Snyder, Nat. Genetics. 26, 283-289, 2000

DISCLOSURE OF THE INVENTION

Problem to be Solved by the Invention

An objective of the present invention is to provide easier, faster, more sensitive and more accurate methods for analyzing interactions between sugar chains and proteins that interact with sugar chains.

Means to Solve the Problems

The present inventors conducted dedicated research to solve the aforementioned problem.

In the methods for immobilizing proteins via their amino groups, crosslinking with a solid phase carrier generally occurs at random sites in the protein. Therefore, there is a certain probability that some molecules will lose their activity, but conversely, there is a high probability that protein activity will be retained (the risk of total destruction of the proteins is small). These properties are extremely useful for the practical use of microarrays for which immobilization of a large number of proteins with different properties, or proteins having unknown properties, is envisioned.

Thus, upon producing lectin microarrays, and after comprehensively considering the usefulness of microarrays in terms of practicality, applicability, quick responsiveness towards the objective subjects of analysis, market competitiveness (including costs), and such, the present inventors judged that methods for immobilizing proteins using their amino groups are currently the most suitable. In the present invention, the optimum conditions for methods for immobilizing proteins via amino groups were examined from multiple perspectives, with the aim of improving the signal-to-noise ratio (S/N ratio) and the protein immobilization density.

As a result, protein samples were immobilized under higher S/N ratio conditions than conventional products by coating the surface of slide glasses with 3-glycidoxypropyl trimethoxysilane (GTMS). Moreover, the present inventors produced a substrate in which a number of reaction vessels were formed by affixing a rubber having a number of holes onto the glass, enabling the accurate filling of the areas around lectin spots with a fluorescence-labeled probe solution. In addition, they attempted to improve the immobilization density of lectins by spotting lectins and washing with PBST, and thereby succeeded in detecting the weak interactions between sugar chains and lectins with greater sensitivity.

In the present invention it is unnecessary to wash and remove the probe solution, procedures which were highly problematic when precisely analyzing data on the interactions between lectins and sugar chains under conditions of equilibrium, and it also became possible to detect weak interactions that would be washed away during the washing in conventional methods.

In this manner, the practical use of lectin arrays became possible by improving the immobilization and detection methods. Specifically, the present invention provides the following (1) to (22) regarding methods for analyzing the interactions between sugar chains and proteins that interact with sugar chains:

(1) a method for analyzing an interaction between a sugar chain and a protein that interacts with a sugar chain, wherein the method comprises the steps of:
  (a) contacting a fluorescently labeled subject sugar chain or subject glycoconjugate with a substrate onto which a protein that interacts with a sugar chain has been immobilized; and
  (b) measuring the intensity of an excited fluorescence after applying an excitation light without washing the substrate;
(2) the method of (1), wherein the substrate onto which the protein that interacts with the sugar chain has been immobilized is a substrate coated with a compound comprising an epoxy group as an active group;
(3) the method of (2), wherein the compound comprising an epoxy group as an active group is 3-glycidoxypropyl trimethoxysilane (GTMS);
(4) a method for analyzing an interaction between a sugar chain and a protein that interacts a with sugar chain, wherein the method comprises the steps of:
  (a) contacting a protein that interacts with a fluorescently labeled sugar chain with a substrate onto which a subject glycoconjugate has been immobilized; and
  (b) measuring the intensity of an excited fluorescence after applying an excitation light without washing the substrate;
(5) the method of (4), wherein the substrate onto which the subject glycoconjugate has been immobilized is a substrate coated with a compound comprising an epoxy group as an active group;
(6) the method of (5), wherein the compound comprising an epoxy group as an active group is 3-glycidoxypropyl trimethoxysilane (GTMS);
(7) a method for analyzing an interaction between a sugar chain and a protein that interacts with a sugar chain, wherein the method comprises the steps of:
  (a) contacting a subject glycoconjugate with a substrate onto which a protein that interacts with a region other than a sugar chain of a glycoconjugate has been immobilized;
  (b) contacting a fluorescently labeled protein that interacts with a sugar chain with the substrate obtained in step (a); and
  (c) measuring the intensity of an excited fluorescence after applying an excitation light without washing the substrate;
(8) the method of (7), wherein the substrate onto which the protein that interacts with a region other than a sugar chain of a glycoconjugate has been immobilized is a substrate coated with a compound comprising an epoxy group as an active group;
(9) the method of (8), wherein the compound comprising an epoxy group as an active group is 3-glycidoxypropyl trimethoxysilane (GTMS);
(10) the method of any one of (7) to (9), wherein the protein that interacts with a region other than a sugar chain of a glycoconjugate is an antibody;
(11) the method of any one of (1) to (10), wherein the protein that interacts with a sugar chain is a lectin, an enzymatic protein comprising a sugar-binding domain, a cytokine having an affinity for a sugar chain, or an antibody that interacts with a sugar chain;
(12) the method of any one of (1) to (11), wherein the excitation light is an evanescent wave;
(13) the method of any of (1) to (12), wherein the glycoconjugate is a glycoprotein, a proteoglycan, or a glycolipid;
(14) a substrate coated with a compound comprising an epoxy group as an active group and onto which a protein that interacts with a sugar chain or a protein that interacts with a region other than a sugar chain of a glycoconjugate has been immobilized;
(15) the substrate of (14), wherein the compound comprising an epoxy group as an active group is 3-glycidoxypropyl trimethoxysilane (GTMS);
(16) the substrate of (14) or (15), wherein the protein that interacts with a region other than a sugar chain of a glycoconjugate is an antibody;
(17) the substrate of (14) or (15), wherein the protein that interacts with a sugar chain is a lectin, an enzymatic protein comprising a sugar-binding domain, a cytokine having an affinity for a sugar chain, or an antibody that interacts with a sugar chain;
(18) the substrate of any one of (14) to (17), wherein the glycoconjugate is a glycoprotein, a proteoglycan, or a glycolipid;
(19) a method for producing a substrate, wherein the method comprises the steps of:
  (a) coating the substrate with a compound comprising an epoxy group as an active group; and
  (b) immobilizing a protein that interacts with a sugar chain or a protein that interacts with a region other than a sugar chain of a glycoconjugate onto the substrate obtained in step (a);
(20) the method of (19), wherein the protein that interacts with a region other than a sugar chain of a glycoconjugate is an antibody;
(21) the method of (19), wherein the protein that interacts with a sugar chain is a lectin, an enzymatic protein comprising a sugar-binding domain, a cytokine having an affinity for a sugar chain, or an antibody that interacts with a sugar chain; and
(22) the method of any one of (19) to (21), wherein the glycoconjugate is a glycoprotein, a proteoglycan, or a glycolipid.

A: Schematic diagram of a case using a lectin array with a sugar chain as the probe. This can be used for estimating the structure of fluorescently labeled sugar chains. The sugar chain can be fluorescently labeled indirectly.

B: Schematic diagram of a case using a lectin array with a glycoprotein as the probe. This can be used for estimating sugar chain structures on a protein. The sugar chain can be fluorescently labeled indirectly.

C: Schematic diagram of a case using a glycopeptide array with a lectin as the probe. This can be used for estimating sugar chain structures on a fractionated peptide.

D: Schematic diagram of a case using a glycoprotein array with a lectin as the probe. This can be used for estimating sugar chain structures on a two-dimensionally fractionated protein.

E: Schematic diagram of a case using an antibody array with a lectin as the probe. This can be used for estimating sugar chain structures on a crude glycoprotein.

Figure 10:
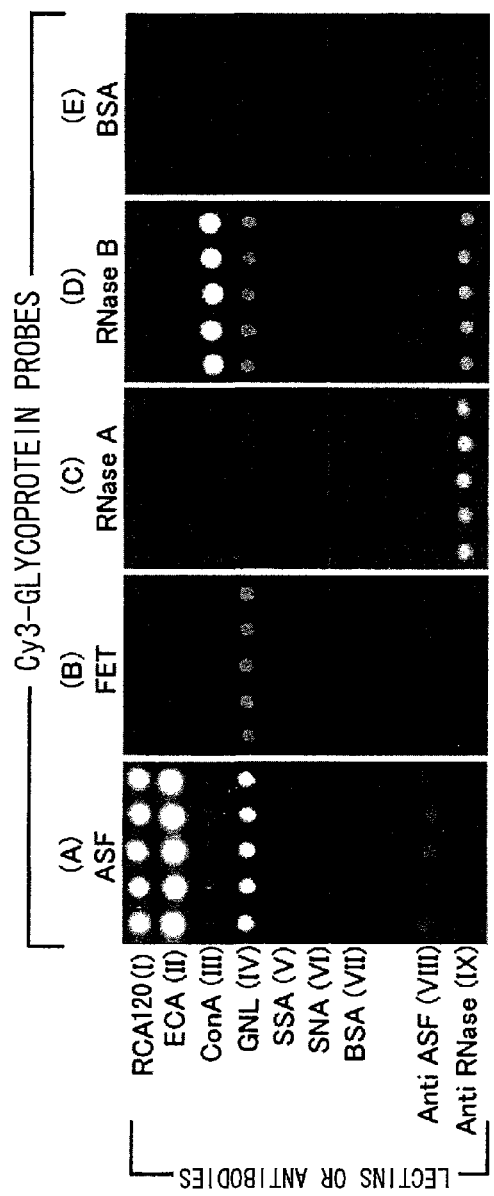

FIG. 10 is a photograph showing an example of a lectin-antibody hybrid array. Specifically, FIG. 10 shows the results of contacting probe solutions of each fluorescently labeled model protein with an array onto which seven types of lectins and two types of antibodies are immobilized, and making post-equilibrium observations using an evanescent excitation-type scanner.

Figure 11:
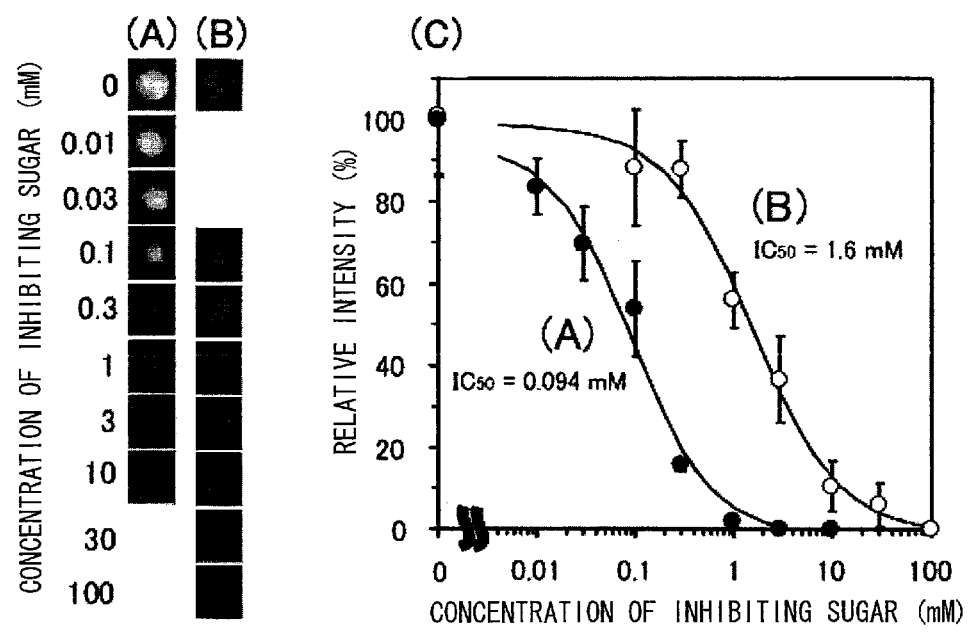

FIG. 11 is a photograph and diagram showing the results of using eight reaction vessels to observe the inhibition of interactions when different concentrations of an inhibiting sugar are present on the same slide glass. (A) Addition of lactose to the binding of RCA 120 and ASF; (B) Addition of mannose to the binding of ConA and RNase B.

Figure 12:
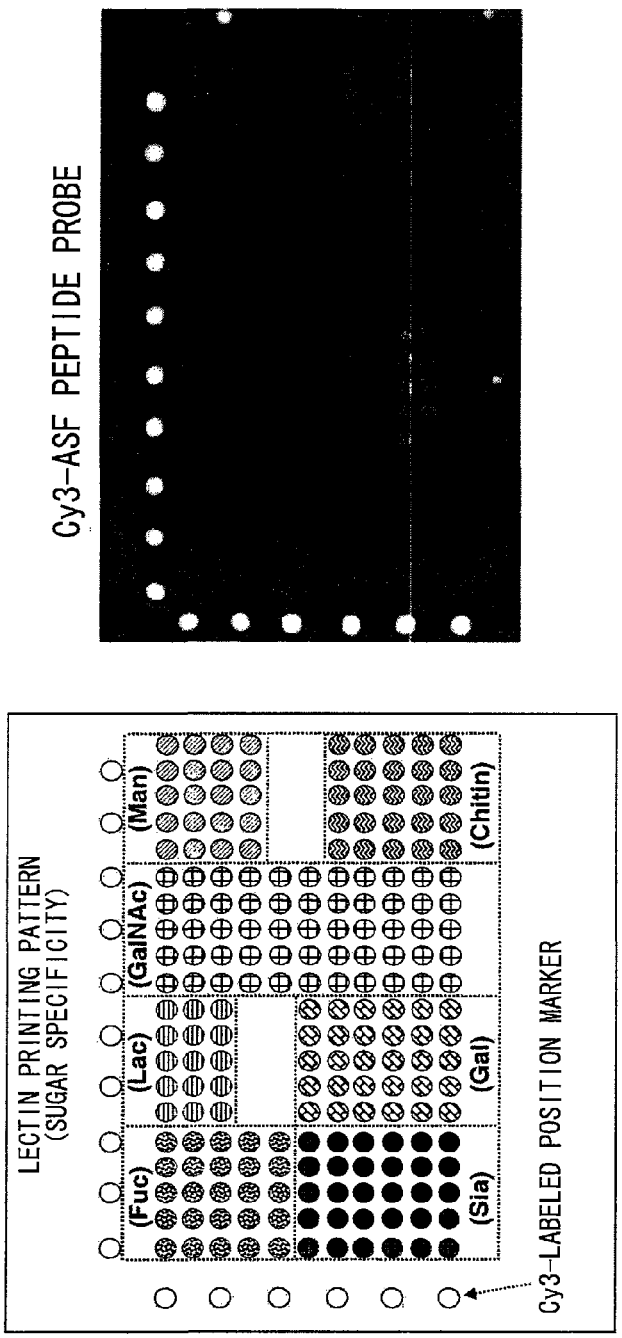

FIG. 12 is a diagram and photograph showing the results of a detection experiment using a glycopeptide array onto which are immobilized HPLC separation fractions of peptide samples derived from mouse liver. In the diagram, Fuc refers to a fucose-recognizing lectin group; Sia refers to a sialic acid-recognizing lectin group; Lac refers to a lactose-recognizing lectin group; Gal refers to a galactose-recognizing lectin group; GalNAc refers to a N-acetyl galactosamine-recognizing lectin group; Man refers to a mannose-recognizing lectin group; and Chitin refers to a chitin-recognizing lectin group.

Figure 13:
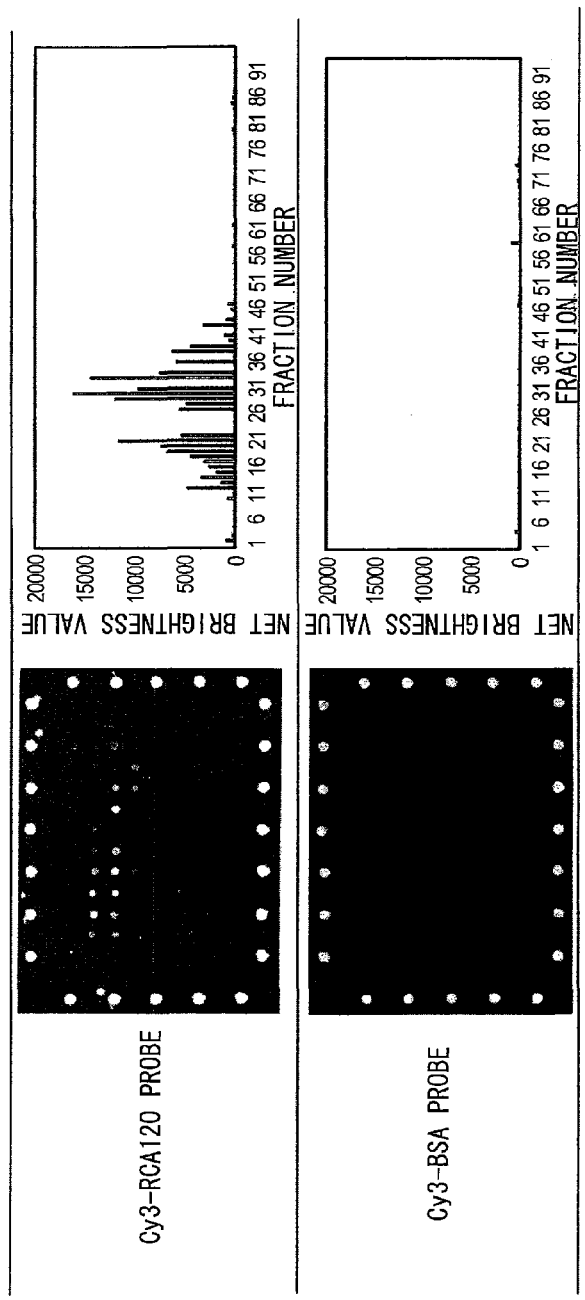

FIG. 13 is a photograph and diagram showing the results of an experiment which uses a glycopeptide probe for lectin array detection.

Figure 14:
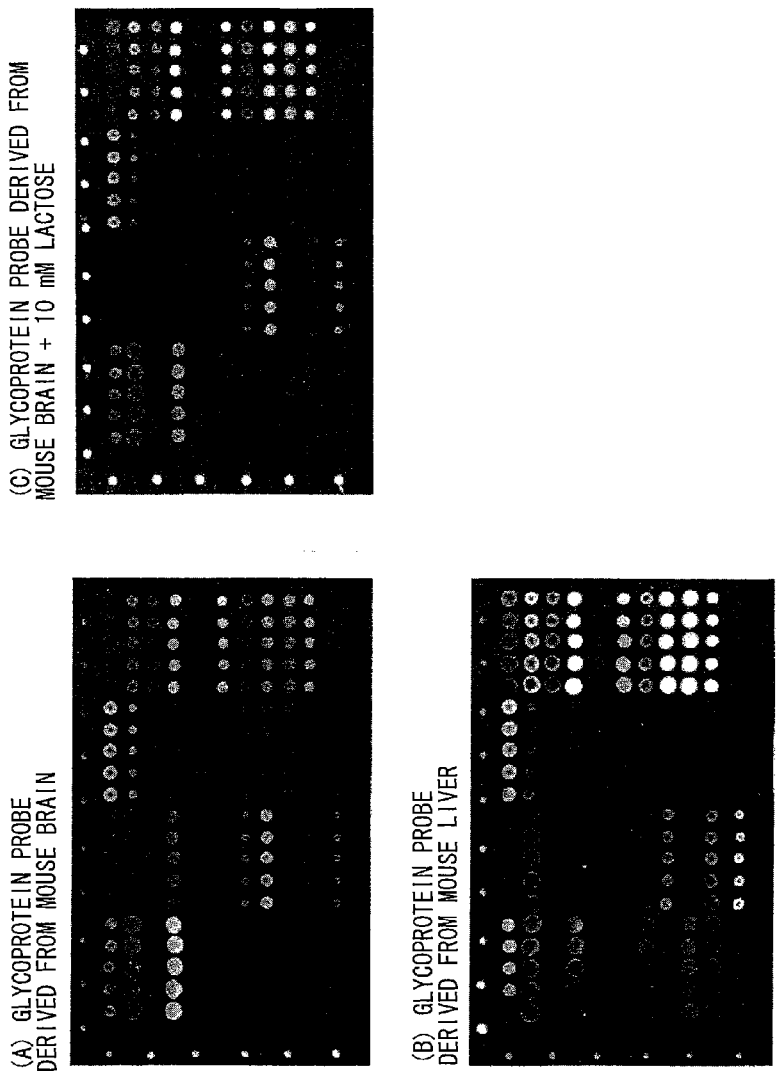

FIG. 14 is a photograph showing the results of lectin array analysis when crude biological samples were made into probes.

BEST MODE FOR CARRYING OUT THE INVENTION

The present invention provides methods for analyzing interactions between sugar chains and proteins that interact with sugar chains. The methods of the present invention comprise a step of contacting a fluorescence-labeled subject sugar chain or subject glycoconjugate with a substrate onto which proteins that interact with sugar chains have been immobilized, and a step of measuring the intensity of excited fluorescence using an excitation light without washing the substrate.

Examples of sugar chains in the present invention comprise glycoprotein-type sugar chains (N-linked sugar chains and O-linked sugar chains), glycolipid-type sugar chains, glycosaminoglycan-type sugar chains, and polysaccharide-derived oligosaccharide chains. In addition, 1) examples of N-linked sugar chains comprise high-mannose, hybrid, and complex N-linked sugar chains; 2) examples of O-linked sugar chains comprise mucin-type (O-GalNAc), O-Fuc-type, O-Man-type, and O-Glc-type O-linked sugar chains; 3) examples of glycolipid-type sugar chains comprise the ganglio-series, globo-series, the lacto-series, and the neolacto-series sugar chains; 4) examples of glycosaminoglycan-type sugar chains comprise hyaluronic acid, keratan sulfate, heparin, heparan sulfate, chondroitin sulfate, and dermatan sulfate; and 5) examples of polysaccharide-derived oligosaccharide chains comprise oligosaccharide chains and such derived from chitin, cellulose, curdlan, laminarin, dextran, starch, glycogen, arabinogalactan, alginic acid, fructan, fucoidan, and xylan.

Examples of other sugar chains comprise M3, MSA, hybrid (monoagalacto, bisect), NA1, NA1 (α1-6Fuc), NA2 (monoagalacto), NA2 (monoagalacto, bisect), NA2, NA2 (α1-6Fuc), A2, NA2 (bisect), NA3, NA3 (α1-6Fuc), NA4, NA4 (α1-6Fuc), NA5 (pentaagalacto, bisect), lactose, GA2, GA1, GM3-NeuAc, GM3-NeuGc, GM1, GM2, GD1a, GD1b, GD3, Gb3, Gb4, Forssman, LNnT, LNT, Galili pentasaccharide, B-hexasaccharide, LNFP-I, LNFP-II (Le$^a$), LNFP-III (Le$^x$), LNFP-II (Le$^b$), A-hexasaccharide, A-heptasaccharide, B-pentasaccharide, 6'-sialyl lactose, pLNH, βGalLac, βGal$_2$Lac, LN3, GN3, GN4, maltotriose, and sialyl Le$^x$.

In addition, in the present invention, glycoconjugate is a generic term for biological macromolecules having a sugar chain. Examples of glycoconjugates of the present invention comprise glycoproteins (also comprising glycopeptides), proteoglycans, and glycolipids.

The proteins of the present invention that interact with sugar chains also comprise peptides that interact with sugar chains. Examples of the proteins of the present invention that interact with sugar chains comprise lectins, enzymatic proteins comprising a sugar-binding domain, cytokines having an affinity for sugar chains, mutants thereof, and antibodies that interact with sugar chains.

Examples of the aforementioned lectins comprise lectins belonging to various molecular families obtained from animals, plants, fungi, bacteria, viruses, etc, and more specifically comprise "R-type lectins" related to the ricin B chain found in all organisms including bacteria; "calnexin-calreticulin" present in all eukaryotes and which is involved in the folding of glycoproteins; calcium-requiring "C-type lectins" widely found in multicellular animals and which comprise many typical lectins such as "selectins" and "collectins"; "galectins" which are widely distributed throughout the animal world and show specificity for galactose; "legume lectins" constituting a large family within the leguminous plants; "L-type lectins" structurally similar to the latter and involved in transport within animal cells; mannose-6-phosphate-binding "P-type lectins" involved in intracellular trafficking of lysosomal enzymes; "annexins" which bind to acidic sugar chains such as glycosaminoglycans; and "I-type lectins" which belong to the immunoglobulin superfamily and comprise "Siglec".

Examples of other lectins comprise ACA (*Amaranthus caudatus* agglutinin), BPL (*Bauhinia purpurea* lectin), ConA (Concanavalin A), DBA (*Dolichos biflorus* agglutinin), DSA (*Datura stramonium* agglutinin), ECA (*Erythrina cristagalli* agglutinin), EEL (*Euonymus europaeus* lectin), GNA (*Galanthus nivalis* agglutinin), GSL I (*Griffonia simplicifolia* lectin), GSL II (*Griffonia simplicifolia* lectin), HHL (*Hippeastrum hybrid* lectin), Jacalin (Jackfruit lectin), LBA (Lima bean agglutinin), LCA (*Lens culinaris* agglutinin), LEL (*Loranthus europaeus* lectin), LTL (*Lotus tetragonolobus* lectin), MPA (*Maclura pomifera* agglutinin), NPA (*Narcissus pseudonarcissus* agglutinin), PHA-E (Phytohemagglutinin), PHA-L (Phytohemagglutinin), PNA (Peanut agglutinin), PSA (*Pisum sativum* agglutinin), PTL-I (*Psophocarpus tetragonolobus* lectin), PTL-II (*Psophocarpus tetragonolobus* lectin), PWM (Pokeweed mitogen), RCA120 (*Ricinus communis* agglutinin), SBA (Soy bean agglutinin), SJA (*Sophora japonica* agglutinin), SNA (*Sambucus nigra* agglutinin), SSA (*Sambucus sieboldiana* agglutinin), STL (*Solanum tuberosum* lectin), TJA-I (*Trichosanthes japonica* agglutinin), TJA-II (*Trichosanthes japonica* agglutinin), UDA (*Urtica dioica* agglutinin), UEA I (*Ulex europaeus* agglutinin), VFA (*Vicia faba* agglutinin), VVA (*Vicia villosa* agglutinin), WFA (*Wisteria floribunda* agglutinin) and WGA (Wheat germ agglutinin).

Examples of the aforementioned enzymatic proteins comprising a sugar-binding domain comprise various types of glycosidases (xylanases, glucanases) and glycosyltransferases (UDP-GalNAc: polypeptide GalNAc transferases). In addition, examples of cytokines having an affinity for sugar chains comprise interleukin-2 (IL-2), interleukin-12 (IL-12), tumor necrosis factor α (TNF-α), and fibroblast growth factor (FGF). In addition, examples of antibodies interacting with sugar chains comprise antibodies against sugar chain-related tumor markers (CA19-9, Forssman antigen, T antigen, Tn antigen, and sialyl T antigen), blood type-related sugar chains (A, B, H, Le$^a$, and Le$^x$ antigens), and differentiation-related antigens (Ii and SSEA-1-4).

In addition, examples of the substrates of the present invention comprise glass, quartz glass, synthetic quartz glass, but are not limited thereto. Moreover, the substrates of the present invention onto which the proteins that interact with sugar chains are immobilized are preferably substrates coated with compounds that comprise an epoxy group as the active group, and onto which proteins that interact with sugar chains are immobilized.

A preferable but non-limiting example of a compound that comprises an epoxy group as the active group is 3-glycidoxypropyl trimethoxysilane (GTMS). Other examples comprise 2-(3,4epoxycyclohexyl)ethyltrimethoxysilane, 3-glycidoxypropylmethyldiethoxysilane, 3-glycidoxypropyltriethoxysilane, or silane coupling compounds comprising a number of epoxy groups at the end of a branched spacer, preferably further comprising polyethylene glycol, proteins, biotin/avidin, and such as a spacer.

Substrates of the present invention, onto which proteins that interact with sugar chains are immobilized, can be produced using the method described below.

Figure 3:
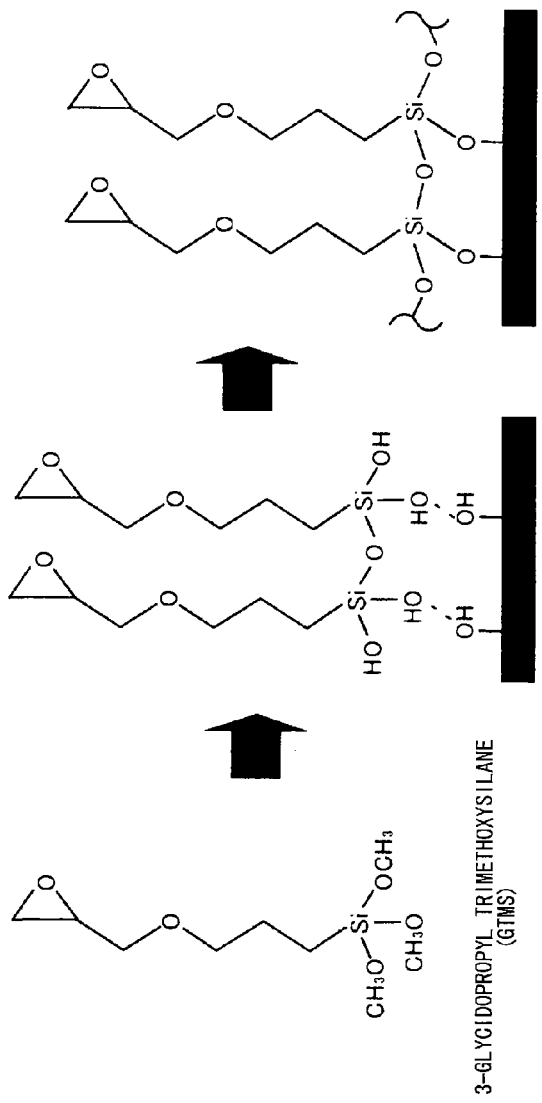
FIG. 3 is a diagram showing the process of reaction of GTMS with a glass surface. The alkoxysilyl groups of GTMS are hydrolyzed by water and become silanol groups. Since these silanol groups are unstable, they partially condense due to changes over time, and form oligomers which subsequently attach to the glass surface via hydrogen bonding. Then, by subjecting the glass to a drying treatment, a dehydration-condensation reaction occurs with the silanol groups on the glass surface, resulting in strong covalent bonding.

First, a compound comprising an epoxy group as the active group is coated onto the substrate. For example, when GTMS is used as the compound comprising an epoxy group as the active group, coating can be carried out using the method described in the Examples. Specifically, the glass surface is treated by immersing a slide glass in a 10% KOH/MeOH solution and allowing it to stand for one hour while the container is shaken. After washing with a sufficient amount of purified water (MilliQ water), the slide glass is dried in an oven at 60° C. Next, the slide glass is immersed in a 2% GTMS acetone solution and allowed to react in the dark for one hour while the container is shaken. The alkoxysilyl groups of GTMS are hydrolyzed by water and become silanol groups. Since these silanol groups are unstable, they partially condense over time and form oligomers that subsequently attach to the glass surface via hydrogen bonding. After the reaction, the slide glass is dried for eight hours in an oven at 110° C. The drying treatment causes a dehydration-condensation reaction with the silanol groups on the glass surface, resulting in strong covalent bonding. The sequence of a GTMS coating method is shown in FIG. 3

Next, the proteins that interact with sugar chains are immobilized onto the substrate, which is coated with a compound that comprises an epoxy group as the active group. Specifically, immobilization can be performed by spotting compounds which comprise amino groups as active groups onto said substrate and allowing reaction. STAMPMAN, from Nippon Laser Electronics Ltd., or such can be used as the spotter. When a compound that comprises an amino group as the active group is a lectin, the concentration of the spotted lectin is preferably 1 mg/mL or more. Further more preferably, unbound lectin can be removed after the spotting treatment by washing using PBS comprising Tween20 (PBST).

The aforementioned substrates onto which the proteins that interact with sugar chains are immobilized are preferably substrates that constitute a number of reaction vessels. More preferably, they are substrates that constitute a number of reaction vessels by affixing a rubber having a number of holes. As an example of this, eight reaction vessels are produced by affixing an 8-hole rubber, designed and developed by the present inventors, to a given position on a slide glass onto which proteins that interact with sugar chains have been immobilized, as described in the Examples. This 8-hole rubber has eight rectangular holes in an orderly arrangement and can form eight reaction vessels when affixed to a slide glass. Filling these reaction vessels with a fluorescence-labeled probe solution enables smooth contact with the proteins that interact with sugar chains. In addition, these reaction vessels are not limited to 8-hole rubbers and, for example, reaction areas can also be formed by coating non-spotting areas of the glass surface with water repellants. More preferably, a large number of reaction areas are formed. The present invention can also be used with multiple types of proteins that interact with sugar chains being spotted onto the same substrate.

In the methods of the present invention, a fluorescence labeled subject sugar chain or subject glycoconjugate is contacted with a substrate, onto which substrate the aforementioned proteins that interact with sugar chains are immobilized.

In the present invention, examples of fluorescence labeling agents for the subject sugar chains or subject glycoconjugates comprise 2-aminopyridine, Cy3, Cy3.5, Cy5, tetramethyl rhodamine, various types of fluorescent dyes comprising a fluorescein backbone, the Alexa series of fluorescent dyes manufactured by Molecular Probes Inc., and quantum dot fluorescent dyes, but are not limited thereto provided that the substance has the property of fluorescently labeling a sugar chain.

A subject sugar chain or subject glycoconjugate can be fluorescently labeled either directly or indirectly. A subject sugar chain can be indirectly fluorescently labeled by binding a subject sugar chain to a protein pre-labeled with fluorescence, which interacts with sugar chains.

In addition, a subject glycoconjugate can be indirectly fluorescently labeled by binding a subject glycoconjugate to a protein pre-labeled with fluorescence, which interacts with a portion of the subject glycoconjugate other than a sugar chain (for example, an antibody that interacts with a portion of the subject glycoconjugate other than a sugar chain).

In addition, a subject glycoconjugate can also be indirectly fluorescently labeled by binding a subject glycoconjugate to a protein pre-labeled with fluorescence, which interacts with sugar chains (in this case, of the sugar chains of the subject glycoconjugate, the sugar chain that binds to the substrate is a sugar chain other than the sugar chain onto which the protein that interacts with sugar chains is bound).

For example, when an antibody pre-labeled with fluorescence which interacts with a portion other than a sugar chain of a target glycoconjugate is allowed to act on a crude sample, such as a sample, blood, body fluid, bioextract component, food component, or so on, which comprises the target glycoconjugate sample, the target glycoconjugate can be selectively fluorescently labeled without separating or purifying it from the crude sample. In addition, when a crude sample that has been reacted with an aforementioned antibody, which was pre-labeled with fluorescence, is contacted with a substrate onto which lectins have been immobilized, for example, data on the sugar chains of the target glycoconjugate can be selectively observed.

In the methods of the present invention, the interactions of a subject sugar chain or subject glycoconjugate with each of the proteins that interact with sugar chains are then measured using an excitation light, without washing the substrate.

Since the interactions between subject sugar chains or subject glycoconjugates and the proteins that interact with sugar chains are weak compared to generally well-known protein-protein interactions, there were cases in which a dissociation reaction proceeded between the subject sugar chains or subject glycoconjugates and the proteins that interact with sugar chains as a result of removing the probe solution and the washing operations, and in these cases accurate interaction data under equilibrium conditions could not be obtained.

The present inventors solved the above problem by using an excitation light to measure the intensity of the excited fluorescence, without washing the probe solution. More specifically, this measurement method involves shining an incident excitation light from the substrate side without immobilization, and detecting the excited fluorescence. There is no particular limitation as to the excitation lights of the present invention, and examples comprise a light source spliced from white light, preferably a laser light comprising a single wavelength, and more preferably an evanescent wave. Although an evanescent-type excitation microarray scanner is preferably used to detect the excitation light, a confocal-type microarray scanner can also be used.

For example, when excitation light in an evanescent excitation system is totally internally reflected, a faint light referred to as "evanescent light" permeates from the glass interface at a height of 200 nm to 300 nm (about half the excitation wavelength). When using this evanescent light to excite a fluorescent substance, a solution containing probe molecules is contacted to the top of a slide glass, and fluorescence is observed using an incident excitation light, in which case the probe molecules involved in binding reactions can be selectively observed with hardly any excitement of those probe molecules engaged in Brownian motion.

The methods of the present invention can be used to analyze sugar chain structures by utilizing the interaction between fluorescence-labeled subject sugar chains and substrate-immobilized proteins that interact with sugar chains. Specifically, the methods of the present invention are expected to find application as sugar chain profilers that rapidly and easily carry out analyses of sugar chain structures. For example, the methods of the present invention can be applied to the profiling method described in Protein, Nucleic Acid and Enzyme, Vol. 48, No. 11, supplementary issue of August 2003.

Specifically, the present invention can be used in systems that use a computer to analyze sugar chain structures. By using these systems, the structure of a subject sugar chain can be identified when the structure of the subject sugar chain is known. Even when the structure of the sugar chain is unknown, a characteristic structure present in the subject sugar chain (such as α2-3 sialic acid, α2-6 sialic acid, α1-3 galactose, α1-3 fucose, α1-6 fucose, bisect N-acetylglucosamine, or sulfation) can be predicted or a similarity with sugar chains of known structure can be pointed out. These systems automatically display the structure of a subject sugar chain upon placing a substrate in a microarray scanner apparatus, wherein each of the various proteins that interact with sugar chains and which have been contacted with a fluorescence-labeled subject sugar chain have been immobilized on to the substrate. In the systems of the present invention, the step of contacting a fluorescence-labeled subject sugar chain with a substrate, onto which each of the various proteins that interact with sugar chains have been immobilized, can also be automated. Specifically, by guiding a micro flow path system into the reaction vessels on the substrate, and controlling the type, concentration, and flow rate of the solutions sent into the flow path, the steps of blocking and removing the blocking solution, and the step of contacting the fluorescence-labeled sugar chain solution can be controlled in one dimension. Mass spectrometry or enzyme digestion can also be combined with the systems of the present invention, which is very useful since use of these methods enables data with even greater reliability can be obtained.

Figure 1:
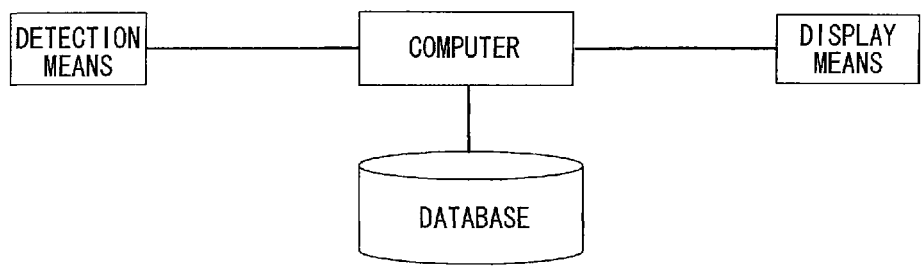
FIG. 1 is a diagram of the composition of a system of the present invention. The Detection Means is a microarray scanner apparatus.

An example of a composition of the system of the present invention is shown in FIG. 1. A system that uses a microarray scanner apparatus is composed of the following:

(a) a storage means (database) which stores data on the interaction of a number of sugar chains with a variety of proteins that interact with a sugar chain;

(b) a detection means which, when a fluorescence-labeled subject sugar chain is contacted with a substrate onto which each of the various proteins that interact with sugar chains are immobilized, detects the intensity of an excited fluorescence after an incident excitation light has been shone on the substrate, without carrying out a washing procedure;

(c) a computer comprising an arithmetic processing means for taking a data combination of the detected fluorescence intensity, comparing it with data stored in (a), and selecting one or a number of sugar chains of known structure having a matching data combination pattern; and (d) a display means for displaying the selection results.

Figure 2:
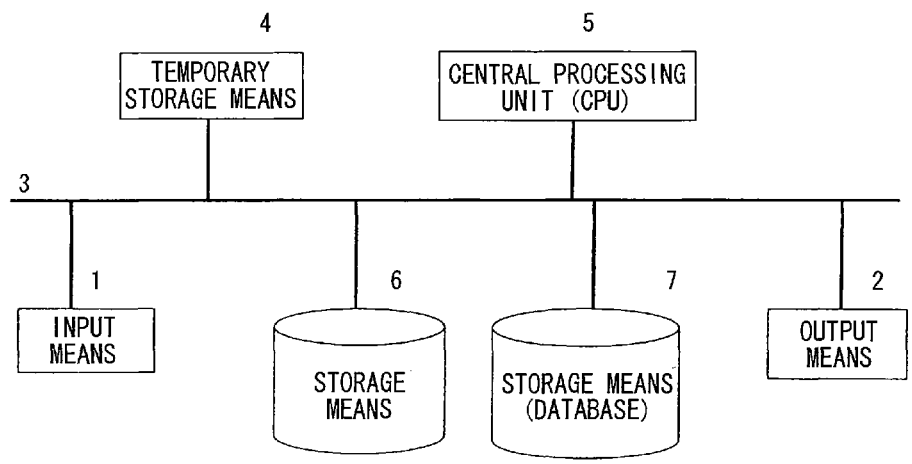
FIG. 2 is a diagram of the composition of a computer in a system of the present invention. Storage Means 6 at least stores Programs 61 to 63 for executing the processes of a system that uses a microarray scanner apparatus. Storage Means (database) 7 stores data on the interaction of a number of sugar chains with various proteins that interact with sugar chains and/or patterns of data combinations of said interaction data.

A database is allowed, both when it is outside the computer, as in FIG. 1, and when it is within the computer, as in FIG. 2.

By using this database, numerous types of sugar chains can be distinguished even with a limited number of lectins. Theoretically, ten types of lectins with different specificity can be used to distinguish $6^{10}=60,466,176$ types of sugar chains, and most of the sugar chain structures that exist in nature can in fact be distinguished.

An example of a composition of a computer in the system of the present invention is shown in FIG. 2. Input Means 1 and Output Means 2 are connected to Bus Line 3. Temporary Storage Means 4 temporarily stores the entered data, the calculated data, and such. Central Processing Unit (CPU) 5 carries out various operations upon receiving commands from the programs of the present invention. Data on the interaction of a number of sugar chains with various proteins that interact with the sugar chains and/or data on patterns of combinations of this interaction data are stored in Storage Means (Database) 7. Fluorescence intensity data obtained by a method or system of the present invention that uses a microarray scanner apparatus, or data obtained from various experimental systems established thus far can be used as the interaction data.

Various types of programs, comprising programs for executing the processes of the present invention, are stored in Storage Means 6. The programs for executing the processes of the present invention at least comprise Program 61, which takes combined data on the entered fluorescence intensities and compares it with combined data stored in a database of data on the interactions of a number of sugar chains with various proteins that interact with sugar chains, and then selects one or a number of sugar chains with known structure that have a matching pattern of combined data (data stored in the database of sugar chains of known structure); the display Program 62; and Program 63 for control thereof.

In the process of comparing data combinations of interaction data, the values of data combinations of interaction data may also be compared. Program 61 may incorporate a function which, for example, takes the values of data combinations of the entered fluorescence intensity and compares them with the values stored in a database of data combinations of interaction data, and then selects one or a number of sugar chains of known structure, based on proximity to these values.

In addition, in the process of comparing the data combinations of interaction data, data combinations of interaction data may be formed into patterns and these patterns may also be compared. In view of this, instead of Program 61 (or together with Program 61), Storage Means 6 may store: Program 61-1, which generates patterns from data combinations of entered fluorescence intensities; Program 61-2, which generates patterns from data combinations of data stored in a database of interactions of a number of sugar chains with various proteins that interact with sugar chains; and Program 61-3, which compares the patterns of data combinations of entered fluorescence intensities with the patterns of data combinations of data stored in a database of interactions of a number of sugar chains with various proteins that interact with sugar chains, and selects one or a number of sugar chains of known structure that have a matching combination pattern. When generating patterns, interaction data can be standardized using a suitable internal standard. A function is incorporated in Program 61-1 and Program 61-2 such that, for example, entering an arbitrary threshold value divides the interaction data into levels within the range of this threshold and encodes them (applies, for example, a different number or a different color to each level).

Program 61-3 is a program that compares patterns obtained by executing Program 61-1 with patterns obtained by executing Program 61-2, and then selects one or a number of sugar chains of known structure that have a matching pattern of data combination. When pattern data are stored in a database, Program 61-3 collates patterns obtained by executing Program 61-1 with patterns stored in the database, and selects one or a number of sugar chains of known structure having a matching pattern. Program 61-3 can incorporate a function that, for example, compares the code of a sugar chain of known structure with the code of a subject sugar chain, and selects a sugar chain of known structure that has a code matching that of the subject sugar chain.

Program 62 displays, for example, the fluorescence intensity data, the interaction data, or the selected sugar chains with known structure, or such.

In the present invention, the aforementioned programs can also be integrated into a single program.

The following provides an example of a flow of processes executed by the systems of the present invention: First, when substrates, onto which are immobilized each of the various proteins that interact with sugar chains and which were contacted with a fluorescence-labeled subject sugar chain, are placed in a microarray scanner apparatus, an incident excitation light is shone onto said substrates and the intensity of the excited fluorescence is detected. When a number of substrates are placed in the microarray scanner apparatus, the number of substrates are sequentially and automatically fixed in the detection unit and scanned. As an example of a processing flow, the fluorescence intensity data is then automatically entered in to a computer. The entered data can be stored in the storage means or temporary storage means of the computer. In addition, fluorescence intensity data may also be stored in a database. By accumulating fluorescence intensity data, a very practical database, of a scale larger than seen before, of data on the interactions of sugar chains with proteins that interact with sugar chains can be constructed.

In the present invention, an arithmetic processing means such as the Central Processing Unit (CPU) can receive a command from Program 62 in the storage means, read the fluorescence intensity data stored in the storage means or temporary storage means, and display said fluorescence intensity data. For example, by taking as standard the fluorescence intensity emitted by a spot of a sample protein that interacts with sugar chains whose properties have already been sufficiently investigated (an internal standard spot), the values of each spot for which the fluorescence value has been adjusted can be displayed. A number of internal standard spots may also be used.

As an example of a processing flow, combined data on the entered fluorescence intensity is then compared with data combinations of data stored in a database of the interactions of a number of sugar chains with various proteins that interact with sugar chains, and one or a number of sugar chains of known structure having a matching combination data pattern are selected. In this processing step, an arithmetic processing means such as the Central Processing Unit (CPU) receives a command from Program 61 in the storage means, reads the data combinations of fluorescence intensities stored in the storage means or temporary storage means and the data combinations of the data stored in a database of interactions of a number of sugar chains with various proteins that interact with sugar chains, compares each of the data combinations, and selects one or a number of sugar chains of known structure having a matching data combination pattern. Data on the selected sugar chain of known structure can be stored in the storage means or temporary storage means of the computer.

When the database is outside of the computer, an arithmetic processing means such as the Central Processing Unit (CPU) receives a command from Program 61 in the storage means, enters the data combinations of data stored in a database of interactions of a number of sugar chains with various proteins that interact with sugar chains, reads the data combinations of fluorescence intensities stored in the storage means or temporary storage means, compares each data combination, and selects one or a number of sugar chains of known structure which have a matching pattern of data combination.

Processes are carried out with a similar flow when using Programs 62-1 to 62-3 instead of Program 61.

As an example of a processing flow, the selection result is then displayed by the display means. In this processing step, an arithmetic processing means such as the Central Processing Unit (CPU) receives a command from Program 62 in the storage means, reads the known structure sugar chain data stored in the storage means or temporary storage means, and displays this data.

The present invention provides methods for analyzing interactions between sugar chains and proteins that interact with sugar chains, which comprise a step of letting a fluorescently labeled protein that interacts with sugar chains contact a substrate onto which a subject glycoconjugate is immobilized, and a step of using an excitation light to measure the intensity of the excited fluorescence, without washing the substrate.

In the present invention, a substrate onto which a subject glycoconjugate is immobilized is preferably a substrate in which a subject glycoconjugate is immobilized onto a substrate coated with a compound having an epoxy group as an active group, and more preferably a substrate in which the compound having an epoxy group as an active group is GTMS. Each step is the same as that of the previously described method. The methods of the present invention are useful as a means for enabling simultaneous investigation, after isolating proteins in a body, of the sugar chain addition status of each protein component in a group of proteins, by examining the sugar chain addition status of a subject glycoconjugate immobilized onto a substrate using fluorescently labeled lectins and such (glycoform analysis). In addition, application to the monitoring of quality control and such of the sugar chain portion of protein formulations and such is expected.

Also, the present invention provides methods for analyzing interactions between sugar chains and proteins that interact with sugar chains, which comprise a step of contacting a subject glycoconjugate with a substrate onto which a protein that interacts with a region other than a sugar chain of the glycoconjugate has been immobilized; a step of letting a fluorescently labeled protein that interacts with sugar chains contact the substrate obtained in this step; and a step using an excitation light to measure the intensity of the excited fluorescence, without washing the substrate.

In the present invention, the substrates onto which a subject glycoconjugate has been immobilized are preferably substrates coated with a compound having an epoxy group as an active group and onto which a subject glycoconjugate has been immobilized, and more preferably they are substrates in which the compound having an epoxy group as an active group is GTMS. In addition, the proteins of the present invention that interact with a region other than a sugar chain of a glycoconjugate are preferably antibodies that interact with a region other than a sugar chain of a glycoconjugate. In addition, the proteins that interact with sugar chains are preferably lectins, enzymatic proteins comprising sugar-binding domains, cytokines having affinity for sugar chains, mutants thereof; or antibodies that interact with sugar chains. Although each step is basically the same as in the previously described methods, a further step is comprised in which a fluorescently labeled protein that interacts with sugar chains is contacted with a substrate, onto which a protein that interacts with a region other than a sugar chain of a glycoconjugate has been immobilized, and which has been contacted with the subject glycoconjugate. In this step, for example, a stock solution or diluted solution of a sample, blood, body fluid, bioextract component, food component, or the like comprising a subject glycoconjugate sample is contacted with a substrate onto which a protein that interacts with a region other than a sugar chain of the glycoconjugate has been immobilized, and after ensuring a sufficient reaction time, components other than the subject glycoconjugate are removed by sufficient washing with PBS or PBST. Following this, a fluorescently labeled probe solution that interacts with the sugar chain portion can be contacted.

The present invention is useful as methods for quickly and easily investigating the sugar chain modification status of a protein of interest from within a mixture of different glycoconjugates, and since the methods observe the sugar chain modification status of a protein of interest, without purifying mixed solutions of various components such as stock solutions, diluted solutions, or such of blood, body fluid, bioextract components, food components, and so on, these methods can conceivably be applied to fields such as those with an understanding of aspects of diagnoses and treatment.

The present invention provides methods for producing a substrate, wherein the methods comprise (a) a step of coating a substrate with a compound comprising an epoxy group as an active group and (b) a step of immobilizing onto the substrate obtained in step (a) a protein that interacts with a sugar chain or a protein that interacts with a region other than a sugar chain of a glycoconjugate. The details of the steps of these methods are as previously described. The present invention also provides substrates produced according to the aforementioned methods.

Specifically, the present invention provides substrates coated with compounds comprising an epoxy group as an active group and onto which a protein that interacts with sugar chains or a protein that interacts with a region other than a sugar chain of a glycoconjugate has been immobilized. The substrates of the present invention are preferably substrates in which the compound comprising an epoxy group as an active group is 3-glycidoxypropyl trimethoxysilane (GTMS). In addition, the substrates of the present invention are preferably substrates in which the proteins that interact with a region other than a sugar chain of a glycoconjugate are antibodies that interact with a region other than a sugar chain of a glycoconjugate, or substrates in which a protein that interacts with sugar chains is a lectin, an enzymatic protein comprising a sugar-binding domain, a cytokine having affinity for sugar chains, mutants thereof, or an antibody that interacts with sugar chains. When the compound comprising an epoxy group as an active group is a lectin, the concentration of the spotted lectin is preferably 1 mg/mL or more, although there are no particular limitations. Furthermore, the substrates are more preferably substrates onto which a lectin has been immobilized by washing with PBST. The substrates of the present invention are preferably substrates in which a number of reaction vessels have been formed.

All prior art documents cited in the present specification are incorporated herein by reference.

EXAMPLES

Hereinbelow, the present invention will be specifically described with reference to Examples, but it is not to be construed as being limited thereto.

Example 1

Analysis of Interactions Between Sugar Chains and Lectins Using a Lectin Array (1) Preparation of Fluorescence-Labeled Glycoprotein Probe (Cy3-ASF)

Fluorescence-labeled glycoprotein probes were prepared by fluorescently labeling asialofetuin (Sigma, hereinbelow ASF) using Cy3 Mono-reactive Dye (Amersham-Pharmacia, hereinbelow Cy3), which is a fluorescent dye with a maximum absorption wavelength of around 550 nm. ASF is known to have three N-linked sugar chains and three O-linked sugar chains per molecule, and a sugar chain structure in which the sialic acid cap of the non-reducing terminal in the sugar chains is partially removed. After preparing ASF in a 0.1 M carbonate buffer (pH 9.3) such that the final concentration is 1 mg/mL, 1 mL was mixed with 1.0 mg of Cy3 powder and allowed to react in the dark for one hour while stirring occasionally.

Next, free Cy3 and Cy3-ASF were separated and recovered by gel filtration chromatography using Sephadex G-25 as the carrier and the concentration and fluorescence labeling efficiency were measured for the purified Cy3-ASF using a spectrophotometer. Yield based on proteins was 35% to 40% and the fluorescence labeling efficiency (number of fluorescent dyes per protein molecule) was approximately 3.0.

(2) Coating of GTMS onto Slide Glasses

Lectins were immobilized onto the glass surface using slide glasses coated with 3-glycidoxypropyl trimethoxysilane (Shin-Etsu Silicone, hereinbelow GTMS) which comprises an epoxy group as the active group (FIG. 3). GTMS coating was carried out using slide glasses manufactured by Matsunami Glass Industry Ltd, according to the following procedure: The slide glasses were immersed in a 10% KOH/MeOH solution and allowed to stand for one hour while shaking the container to treat the glass surface. After washing with a sufficient amount of purified water (MilliQ water), they were dried in an oven at 60° C. Next, the slide glasses were immersed in a 2% GTMS acetone solution and reacted in the dark for one hour while shaking the container. After the reaction, they were dried for eight hours in an oven at 110° C., washed with a sufficient amount of purified water, and dried.

(3) Immobilization of Lectins onto Slide Glasses

Lectins were spotted onto the GTMS-coated slide glasses of (2). STAMPMAN, manufactured by Nippon Laser Electronics Ltd., was used as the microarray spotter and spots with a diameter of approximately 0.6 mm to 0.7 mm were arranged onto the slide glasses by using a stamping pin with a tip diameter of 0.40 mm. Each spotted lectin was dissolved in a pH 7.4 phosphate-buffered saline (hereinbelow PBS) such that the concentration was 1 mg/mL (partially 0.25 mg/mL depending on the lectin). These solutions were placed in each reaction vessel of a 96-well PCR microtiter plate (Corning) in 10 µL aliquots and plates were placed on the microarray spotter.

During the process of immobilizing lectins onto the slide glasses, the following conditions were stored in the memory of the computer attached to the microarray spotter to execute a stamping pin operating program: First, the stamping pin was immersed for one second in the immobilization sample solution contained in the 96-well PCR microtiter plate. It was then lifted out and contacted for one second to a predetermined location on the slide glass surface. After repeating this operation for each spot, and spotting four spots from the same sample solution in a horizontal row, the stamping pin was washed. During the washing step, the tip of the stamping pin was immersed for two seconds in a 0.05% SDS solution, the stamping pin was then dried for 15 seconds in a vacuum apparatus, then after immersion for two seconds in purified water, it was dried for 15 seconds in the vacuum apparatus. After a final immersion for two seconds in ethanol, it was dried for 15 seconds in the vacuum apparatus.

In this Example, a total of five types of proteins were spotted, consisting of four types of lectins having various sugar-binding specificities (RCA12, SSA, xylane-binding domain of xylanase derived from recombinant actinomycetes (hereinbelow XBD), and C-terminal domain derived from recombinant earthworm 29 kDa lectin (hereinbelow EW29 (Ch)) and one type of negative control (bovine serum albumin (hereinbelow BSA)). RCA120 and BSA were purchased from Sigma, SSA was purchased from Seikagaku Corp., and the XBD and EW29 (Ch) used were expressed and purified from *E. coli* in the laboratory of the present inventors.

(4) Blocking of Non-Spotted Surfaces

After immobilizing the lectin solutions onto the glass surfaces, which were reacted for one hour after spot treatment, the unbound lectins were washed. Washing was carried out by pipetting, as though spraying, a PBS solution comprising 0.1% Tween20 (PBST) several times onto the slide glasses, followed by further sufficient washing using PBS.

Figure 4:
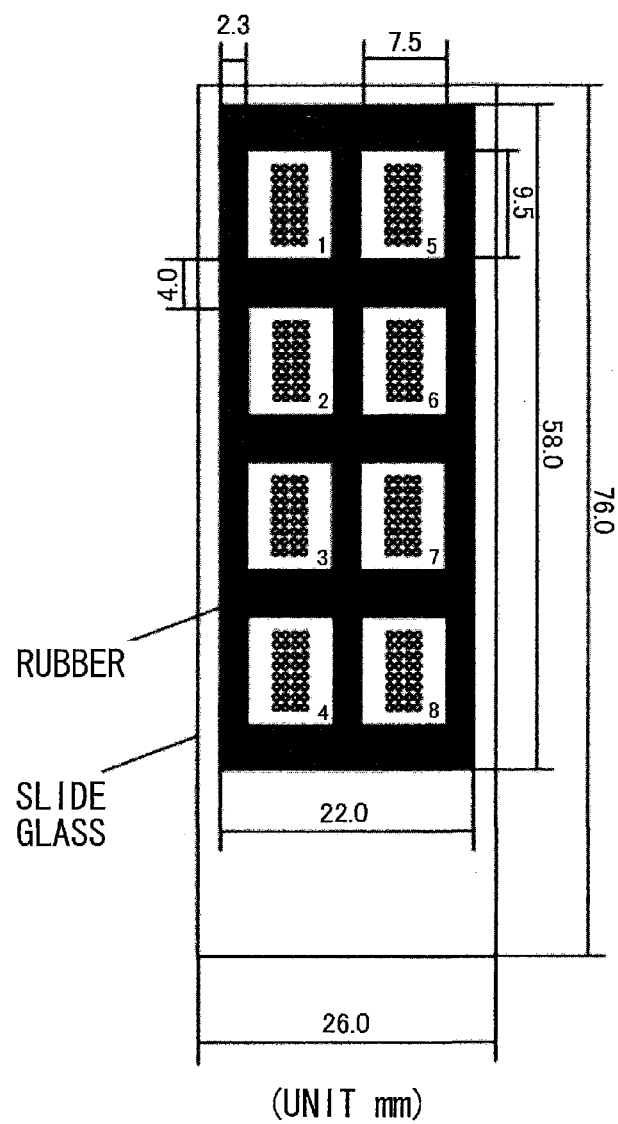
FIG. 4 is a diagram showing a substrate, used in the present Examples, on which eight reaction vessels have been formed. The newly designed 8-hole rubber is 1 mm thick, and by adhering it to a slide glass on a specific adjuster, a fluorescence-labeled probe solution can be accurately filled to the surroundings of the spots. The reaction vessels are optimally filled with 50 µL of sample.

An 8-hole rubber designed and developed by the present inventors was affixed to a predetermined location on the slide glass after lectin immobilization to prepare eight reaction vessels (FIG. 4). This 8-hole rubber is made of a black silicon rubber with a thickness of 1 mm with eight 9.5×7.5 mm rectangular holes are formed in an orderly arrangement therein. When affixed to the slide glasses, the 8-hole rubber can form eight reaction vessels. Adding about 50 µL of sample to a reaction vessel can sufficiently fill the inside with sample solution.

Since epoxy groups, which are active groups, are present on the glass surface in areas other than where lectins were spotted, a blocking procedure was carried out on the non-spotted surfaces. High-purity BSA (Sigma) was used as the blocking agent. Blocking of the non-spotted surfaces on the slide glass was carried out by filling the eight reaction vessels with 50 µL each of a PBS solution comprising 1% BSA and allowing the vessels to stand for one hour at 4° C. in a storage container with humidity maintained at 90% or more. Care was taken to prevent the glass surface from drying out during the reaction.

Next, the blocking solution was removed from the slide glasses, the glass surfaces were sufficiently washed using PBS, and the moisture was eliminated. To prevent the protein denaturation caused by the drying out of the glass surface and the increase of the background that accompanies drying, the experiment was moved on to the next procedure as soon as possible after protein immobilization.

(5) Addition of the Probe Solution and Scanning

A fluorescence-labeled glycoprotein probe solution, the interaction analysis of which is desired, was added to the reaction vessels on the lectin-immobilized slide glasses prepared in (4). The fluorescence-labeled glycoprotein probes were prepared by dissolution in PBS such that the final concentration was 10 μg/mL, and 50 μL was dropped into each reaction vessel.

The reaction vessels were left to stand until the lectin-sugar chain reaction had reached equilibrium, then an excitation light was injected from the edge of the slide glasses using a GTMAS Scan III (Nippon Laser Electronics), which is an evanescent excitation-type microarray scanner, and the emitted fluorescent light generated by excitation was detected using an ICCD (charge coupled device with image intensifier) camera positioned on the lower surface of the slide glasses. Fluorescent images corresponding to nearly the entire surface of the slide glasses were scanned, and the obtained images were saved as TIFF files (approximately 100 megabytes per image). The parameters during scanning were standardized as a gain of "5000 times", number of integration of "four times" and an exposure time of "33 msec".

(6) Digitization of the Scanned Images

Array-Pro Analyzer (Version 4.0 for Windows (registered trademark), Media Cybernetics), which is a commercially available analysis software for microarrays, was used to digitize the scanned images. The brightness of each spot was calculated using the aforementioned analysis software, and the brightness of the non-spotted areas was used as a background value. The difference obtained by subtracting the background value from the brightness of each spot was defined as the net brightness value, and mean values and standard deviations were calculated for each horizontal row of four spots derived from the same sample.

Subsequently, probe binding to each lectin sample was evaluated using this mean brightness value of the four spots derived from the same sample. The performance of each lectin array shown below was evaluated after going through the series of operations (2) to (6).

(7) Evaluation of the Performance of GTMS-Coated Slide Glasses

The performance of the GTMS-coated slide glasses, prepared as described above, was evaluated by comparison with existing slide glasses (six types). Specifically, Cy3-prelabeled lectins (100 μg/mL) were immobilized in the form of an array onto each surface-coated slide glass, and after having gone through steps (3) to (6), the S/N ratios were calculated from the brightness value of the spotted areas (S) and the brightness value of the non-spotted areas (N). As a result, as shown in Table 1, although the brightness value of the GTMS-coated slide glasses prepared in step (2) remained at around one-half that of slide glass A, which showed the highest brightness value, since the background is extremely low, its S/N was 16.1 and showed the best value from among the slide glasses evaluated this time.

TABLE 1

PERFORMANCE EVALUATION OF EACH SLIDE GLASS
100 μg/ml Cy3 RCA-120 in 30% glycerol/PBS

|  | MEAN VALUE OF 4 SPOTS (GAIN × 1000)* | MEAN VALUE OF 4 BLANKS (GAIN × 1000) | S/N RATIO |
|---|---|---|---|
| COMMERCIALLY AVAILABLE SLIDE GLASS A | 60617 | 5971 | 10.2 |
| COMMERCIALLY AVAILABLE SLIDE GLASS B | 52059 | 4013 | 13.0 |
| COMMERCIALLY AVAILABLE SLIDE GLASS C | 36462 | 2865 | 12.7 |
| GTMS SLIDE GLASS | 28220 | 1753 | 16.1 |
| COMMERCIALLY AVAILABLE SLIDE GLASS D | 13838 | 4520 | 3.1 |
| COMMERCIALLY AVAILABLE SLIDE GLASS E | 12802 | 3105 | 4.1 |
| COMMERCIALLY AVAILABLE SLIDE GLASS F | 5902 | 1621 | 3.6 |

Figure 5:
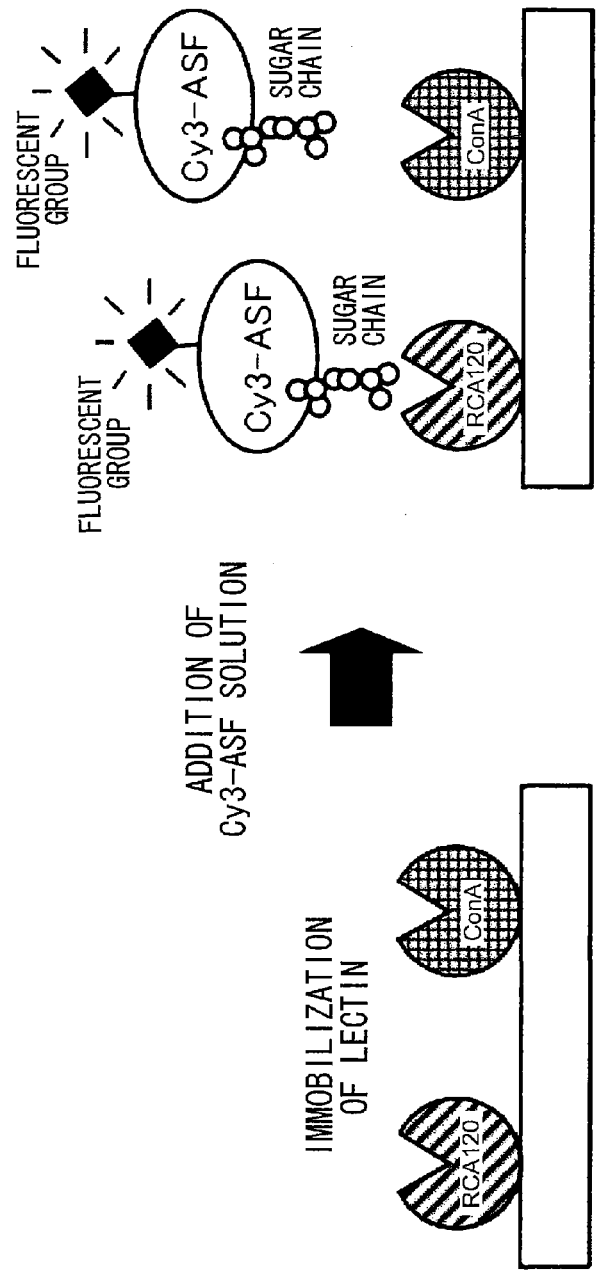
FIG. 5 is a conceptual diagram of a lectin array performance experiment in which a Cy3-ASF solution is added to an array onto which two types of lectin have been immobilized.
Figure 6:
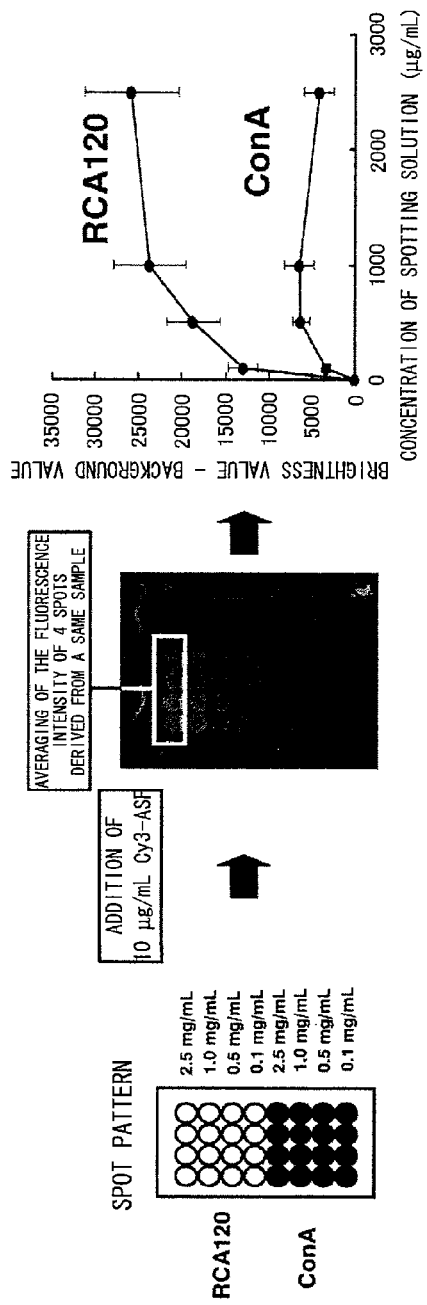
FIG. 6 is a diagram and a photograph showing the relationship between the concentration of the lectin solution at the time of immobilization and the fluorescence intensity of the spots. When detecting lectin-sugar chain interactions with a high affinity constant, setting the concentration of the spotted lectin samples to a high concentration of 1 mg/mL or more was revealed to be effective in improving the signal intensity.

*COMPARISON OF THE MEAN BRIGHTNESS VALUES OF THE SAME Cy3-LABELED LECTIN SPOTS (8) Study of the Concentrations of Immobilized Lectins on the Arrays (FIGS. 5 and 6)

RCA-120 and ConA are typical lectins known to have high affinity for complex sugar chains and high-mannose sugar chains, respectively. These lectins were prepared at various concentrations and spotted in the form of an array, with four spots of the same sample arranged horizontally. 50 μL, of 10 μg/mL Cy3-ASF were dropped into each reaction vessel of these arrays, binding reactions were let to occur, and fluorescence was observed with a scanner.

As was previously described, ASF is known to have three N-linked sugar chains and three O-linked sugar chains per molecule, and a sugar chain structure in which the sialic acid cap of the non-reducing terminal in the sugar chains is removed, resulting in a protruding lactosamine structure. Therefore, in an experimental system in which Cy3-ASF was added to lectin arrays onto which RCA-120 and ConA were immobilized, it was predicted that RCA-120 would show an extremely strong affinity, while ConA would show a weak affinity.

The experiment results suggest that the RCA-120 spots emitted an intense fluorescence, while the ConA spots only showed a fluorescence intensity of about one-third that of the RCA-120 spots under the same conditions. ConA was thought to bind, albeit weakly, to ASF, which has complex sugar chains, because it can bind to the biantennary N-linked sugar chains, which are considered present in small amounts, even though it cannot bind to the triantennary sugar chains that are mainly present in ASF. In addition, this data also showed that the standard deviation (SD) for four spots derived from the same sample is approximately ±20% (FIG. 6).

Next, representing the relationship between lectin concentration at the time of spotting and fluorescence intensity as a graph revealed a positive correlation between the two, revealing that signal intensity can be effectively improved by increasing the concentration of the lectin sample to be spotted to 1 mg/mL or more. Specifically, the results revealed that interactions between lectins and sugar chains with a small affinity constant (weak binding) can be detected by increasing the concentration of the immobilized lectin (FIG. 6).

(9) Evaluation of the Performance of the Lectin Array

A total of five types of proteins consisting of four types of lectins having various sugar specificities (RCA-120, SSA, XBD, and EW29 (Ch)) and one type of negative control (BSA) were spotted in the form of an array, with four spots arranged horizontally for the same sample. 50 μl of 10 μg/mL Cy3-ASF was dropped to each of these arrays and the fluorescence was observed with a scanner.

Figure 7:
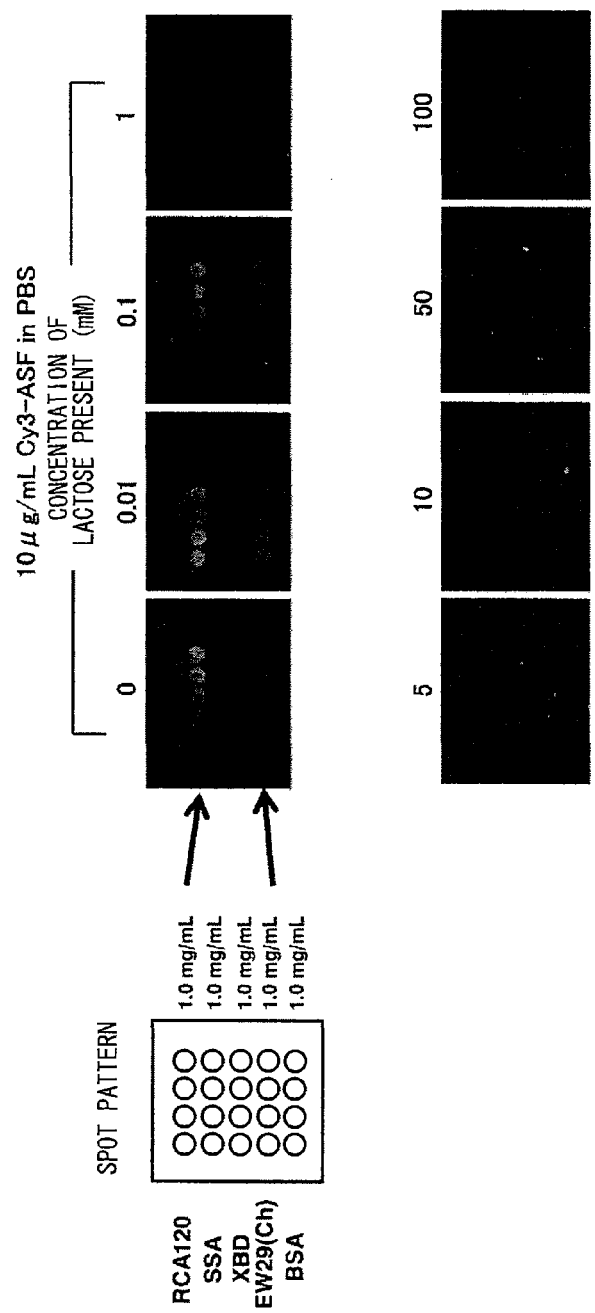
FIG. 7 is a diagram and a photograph showing the detection of lectin-sugar chain interactions and the effect of an inhibiting sugar on the interaction. Strong fluorescence was observed in RCA120 spots, while moderate fluorescence was observed in EW29(Ch) spots.

As a result of this experiment, fluorescent signals were observed for the spots of two types of lectins, RCA-120 and EW29 (Ch), which were confirmed by FAC to have an affinity for the lactosamine structure (FIG. 7). In addition, when the fluorescence intensities of each were compared, a strong fluorescence was observed for RCA-120 spots while an intermediate fluorescence was observed for EW29 (Ch) spots, matching the FAC analysis data.

Figure 8:
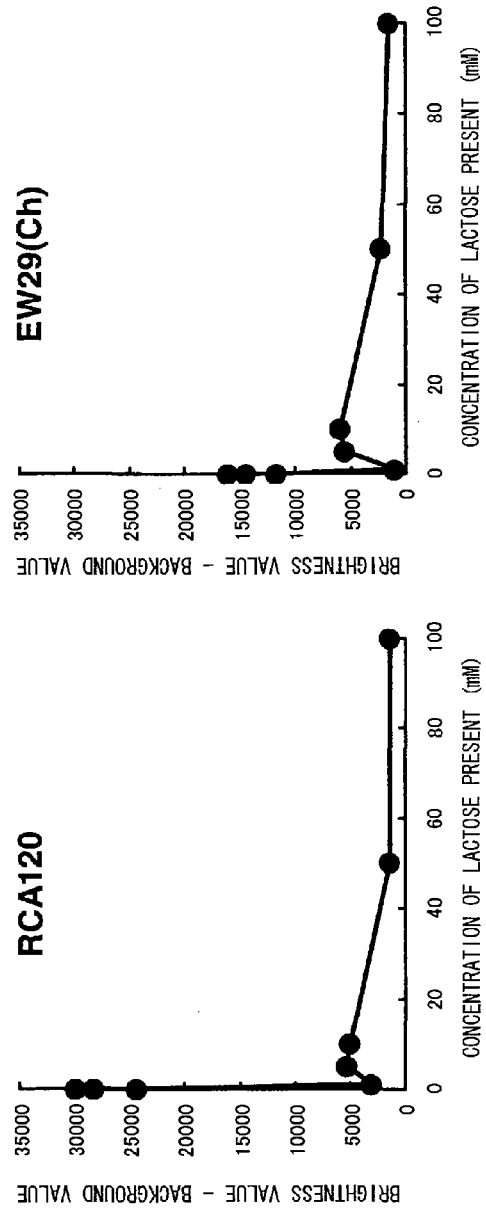
FIG. 8 is a diagram showing the effect of an inhibiting sugar on the lectin-sugar chain interaction as a graph. The experiment was carried out in the presence of lactose (a competitively inhibiting sugar). Since the fluorescence intensity of the spots decreases as the concentration of lactose (competitively inhibiting sugar) increases, binding of the fluorescent glycoprotein probe was confirmed to be a sugar-specific binding reaction between the lectin and the sugar chain.

In addition, when a similar experiment was conducted on an array under the same conditions in the presence of lactose (a competitively inhibiting sugar), the fluorescence intensity of the spots was observed to decrease as the concentration of inhibiting sugar increased (FIG. 8). From the above, the binding to fluorescent glycoprotein probes was confirmed to be due to a sugar-specific binding reaction between lectins and sugar chains.

Example 2

Application to Other Sugar Chain-Related Arrays

Figure 9:
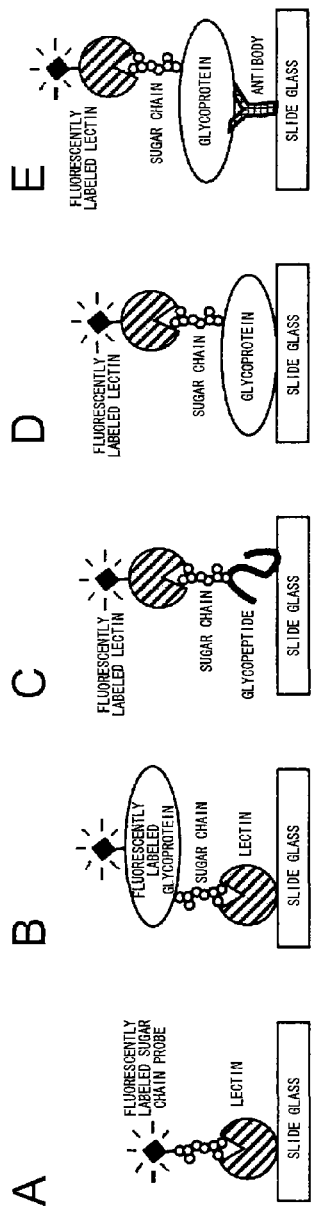
FIG. 9 is a schematic diagram of the interactions between each sugar chain-related array and a sugar chain.

Examples of a sugar chain-related array comprise the following five types: lectin arrays that use sugar chains as probes, as well as lectin arrays that use glycoproteins as probes, glycopeptide arrays that use lectins as probes, glycoprotein arrays that use lectins as probes, and antibody arrays that use lectins as probes. A schematic diagram of each type of sugar chain-related array and the sugar chain interactions is shown in FIG. 9.

Fluorescence intensity data obtained using each array are encoded. Since the numerical value of the brightness value is incorporated in 16 bits, it is a value between zero and 65,355. Given this, coding in six levels, from "0" to "5" at intervals of 10,000, was carried out by classifying the "brightness value—background value" values under a gain of "1000 times". When brightness signal values under a gain of "1000 times" are saturated, observation is carried out after lowering the gain and values are converted to those under a gain of "1000 times". Whether or not a signal value is saturated can be determined by judging whether or not a linear correlation between gain values and signal strength is maintained when the gain values are modified.

| Current Threshold Values (brightness value - background value) | |
| --- | --- |
| 0-10000 | Level 0 |
| 10001-20000 | Level 1 |
| 20001-30000 | Level 2 |
| 30001-40000 | Level 3 |
| 40001-50000 | Level 4 |
| 50001 or more | Level 5 |

Example 3

Analysis by an Array in which Lectin-Antibody were Spotted in a Same Area (FIG. 10)

1. Materials and Methods
(1) Preparation of a Fluorescently Labeled Probe for a Model Glycoprotein In this example experiment, six types of lectins with various sugar-binding specificities (RCA120, ECA, ConA, GNA, SSA, and SNA) were selected as lectins to be immobilized onto a lectin array. In addition, BSA, which is a protein that does not bind to sugar chains, was selected as the negative control. Also, in this experiment, two types of antibodies, anti-fetuin antibody and anti-RNase antibody, which recognize the core protein portion of the probe, were spotted in the same area as the lectins. GNA and SNA were purchased from Vector; BSA was purchased from Sigma; and RCA120, ECA, ConA, and SSA were purchased from Seikagaku Corp.

Fluorescently labeled model glycoprotein probes were prepared by fluorescently labeling proteins such as ASF, FET, and bovine pancreas-derived ribonuclease B (RNase B) or proteins such as bovine pancreas-derived ribonuclease A (RNase A) and BSA for the negative controls (all purchased from Sigma) using Cy3 Mono-reactive Dye (Amersham-Pharmacia, hereinbelow referred to as Cy3), which is a fluorescent dye with a maximum absorbance wavelength in the vicinity of 550 nm. When preparing the probes, the above-mentioned proteins were prepared in a 0.1 M carbonate buffer (pH 9.3) such that the final concentration was 1 mg/mL, and they were then mixed with 1.0 mg of Cy3 powder and allowed to react in the dark for one hour while stirring occasionally. Cy3-labeled proteins were purified by gel filtration chromatography using Sephadex G-25 as the carrier.

(2) Coating of GTMS onto Slide Glasses

Lectins were immobilized onto the glass surface using slide glasses coated with 3-glycidoxypropyl trimethoxysilane (Shin-Etsu Silicone, hereinbelow GTMS) which comprises an epoxy group as the active group (FIG. 3). GTMS coating was carried out using slide glasses manufactured by Matsunami Glass Industry Ltd, according to the following procedure: The slide glasses were immersed in a 10% KOH/MeOH solution and allowed to stand for one hour while shaking the container to treat the glass surface. After washing with a sufficient amount of purified water (MilliQ water), they were dried in an oven at 60° C. Next, the slide glasses were immersed in a 2% GTMS acetone solution and reacted in the dark for one hour while shaking the container. After the reaction, they were dried for eight hours in an oven at 110° C., washed with a sufficient amount of purified water, and dried.

(3) Production of a Lectin Array

Lectins were spotted onto the GTMS-coated slide glass prepared in (2) to produce a lectin array. STAMPMAN, manufactured by Nippon Laser Electronics Ltd., was used as the microarray spotter and spots with a diameter of approximately 0.5 mm were laid on the slide glass using a stamping pin with a tip diameter of 0.40 mm. During the process of immobilizing lectins onto the slide glasses, the following conditions were stored in the memory of the computer attached to the microarray spotter to execute a stamping pin operating program: First, the stamping pin was immersed for one second in the immobilization sample solution contained in the 96-well PCR microtiter plate. It was then lifted out and contacted for one second to a predetermined location on the slide glass surface. After repeating this operation for each spot, and spotting six spots from the same sample solution in a horizontal row, the stamping pin was washed. During the washing step, the tip of the stamping pin was immersed for two seconds in a 0.05% SDS solution, the stamping pin was then dried for 15 seconds in a vacuum apparatus, then after immersion for two seconds in purified water, it was dried for 15 seconds in the vacuum apparatus. After a final immersion for two seconds in ethanol, it was dried for 15 seconds in the vacuum apparatus.

(4) Blocking of Non-Spotted Surfaces

To prepare eight reaction vessels, an 8-hole silicon rubber was affixed to the slide glass onto which lectins were spotted in the aforementioned procedure. By filling the reaction vessels with a PBS solution containing 0.1% Tween 20 (PBST), the excess lectin that did not bind to the solid layer of the slide was washed away and removed. Next, surfaces not spotted with lectins were blocked by filling each reaction vessel with 200 μL of a PBS solution into which 1% BSA was dissolved, and allowing this to stand for one hour at 4° C. in a storage vessel in which the humidity was maintained at 90% or more.

(5) Addition of Probe Solutions and Scanning

50 μL, of each fluorescently labeled glycoprotein probe solution, prepared at approximately 100 ng/mL, was added to each reaction vessel of a slide glass for which blocking was complete, and the probe solutions were then contacted with the array.

The reaction vessels were left to stand until the lectin-sugar chain reaction had reached equilibrium, then an excitation light was injected from the edge of the slide glasses using a GTMAS Scan III (Nippon Laser Electronics), which is an evanescent excitation-type microarray scanner, and the emitted fluorescent light generated by excitation was detected using an ICCD (charge coupled device with image intensifier) camera positioned on the lower surface of the slide glasses. Fluorescent images corresponding to nearly the entire surface of the slide glasses were scanned, and the obtained images were saved under a TIFF file format. The parameters during scanning were standardized as a gain of "4000 times", number of integration of "eight times" and an exposure time of "110 msec".

(6) Digitization of the Scanned Images

Array-Pro Analyzer Ver 4.5 (Media Cybernetics), which is a commercially available analysis software for microarrays, was used to digitize the scanned images. The brightness of each spot was calculated using the aforementioned analysis software, and the brightness of the non-spotted areas was used as a background value. The difference obtained by subtracting the background value from the brightness of each spot was defined as the net brightness value, and mean values and standard deviations were calculated for each horizontal row of five spots derived from the same sample.

Subsequently, probe binding to each lectin sample was evaluated using this mean brightness value of the five spots derived from the same sample.

2. Results and Discussion

In this experiment, an array was composed in which lectins with diverse specificities were arranged in rows, and performance as a lectin array was evaluated from the fluorescence pattern of each lectin spot when glycoprotein probes of known sugar chain structure were applied. Also, this experiment aimed to simultaneously acquire information on the core protein portion of the probes, and an array was produced in which antibodies recognizing the core protein portion of the glycoprotein probes were spotted together with the lectins. As model glycoproteins, the combination of ASF and FET and the combination of RNase A and RNase B, which are proteins having identical structure in the core protein portion but different structures in the modified sugar chain portion, were selected.

Experiments (A) and (B) compared the sugar chain profiles of ASF and FET, which were used as probes (FIGS. 10A and 10B). FET is known to have three N-linked sugar chains and three O-linked sugar chains per molecule, with the non-reducing terminal of each sugar chain structure highly modified with sialic acid. On the other hand, ASF is a protein in which the terminal sialic acids of the FET sugar chain have been removed by enzyme or acid treatment, exposing the lactosamine structures. Consequently, it was predicted that when an ASF probe was used, the RCA120 and ECA spots, which recognize lactosamine, would be observed; and that when an FET probe was used, the SSA and SNA spots, which recognize sialic acid, would be observed. It was predicted that binding to the antibody spots would be observed for both probes, since FET and ASF have an identical core protein portion. As a result of the experiment, extremely bright RCA120 and ECA spots were detected with the ASF probe, which has terminal lactosamine structures (FIG. 10A), however, these RCA120 and ECA spots were extremely dark with the FET probe, in which the lactosamine structures were capped with sialic acid (FIG. 10B). This result coincided with conventional findings that RCA120 and ECA strongly recognize lactosamine structures, and that when the terminal lactosamine structures are capped with sialic acid, the affinity decreases considerably. In addition, in experiment (B), spots of SSA and SNA, which are sialic acid-recognizing lectins, were observed in response to the presence of sialic acids, which are characteristic of the FET probe (FIG. 10B). A weak fluorescence was observed for ConA spots in both experiments (A) and (B) (FIGS. 10A and 10B). This was believed to be because binding to the biantennary sugar chains present in a small amount is enabled, although affinity for the triantennary sugar chains that are mainly present in N-linked sugar chains is low. Fluorescence of the FET antibody spot, which recognizes a common core protein portion, was observed in experiments (A) and (B) (FIGS. 10A and 10B).

In experiments (C) and (D), differences in the sugar chain profiles of the RNase A and RNase B probes were compared (FIGS. 10C and 10D). It is known that RNase B has a one high mannose-type N-linked sugar chain per molecule, and that RNase A has a core protein portion identical to that of RNase B, but no sugar chain. It was predicted that when these probes were contacted with a lectin array, both probes would show an affinity for the anti-RNase antibody spots, but with a difference in reactivity to the lectin spots (the RNase B probe shows an affinity for mannose-recognizing lectins such as ConA, while RNase A does not). In the results of these experiments regarding antibody reactivity binding with the RNase antibody, which recognizes a common core protein portion in both probes, was observed. On the other hand, regarding reactivity to lectins, binding of the ConA spot was observed with RNase B, which has a high mannose structure, however, with RNase A, which does not have any sugar chains, no fluorescence resulting from binding was observed in the lectin spots. In experiment (E), BSA, which is a protein without any sugar chains, was used as a negative control. As predicted, with the BSA probe, binding was observed for neither the antibody nor the lectin spots (FIG. 10E).

Through experiments (A) to (E), profiles reflecting the sugar-binding specificity of lectins were rapidly obtained from extremely small amounts of protein samples (FIGS. 10A to 10E). In addition, in this experiment lectins and antibodies were spotted on the same array, enabling information on the core protein portion and the modified sugar chain portion of glycoproteins to be obtained on a single slide, simultaneously and in parallel. Performing simultaneous and parallel analyses on a single slide brings about the advantage of enabling observations under uniform experimental conditions (such as temperature and reaction time) for each vessel.

Example 4

Analysis of Inhibition Concentration Using a Lectin Array (FIG. 11)

1. Materials and Methods

Inhibition experiments using a competitively inhibiting sugar were conducted to confirm that the binding between the lectins and probe molecules observed in the previous experiments consisted of specific binding mediated by sugar chains. In experiment (A), an array was formed by spotting RCA120 into the eight reaction vessels on a slide glass, and then eight types of ASF probe solution, in which the concentration of a competitively inhibiting sugar (lactose) was modified, were simultaneously contacted with the array, and inhibition of the binding reaction was observed (FIG. 11A). In experiment (B), inhibition of binding was observed by a similar procedure, using ConA as the immobilized lectin, RNase B as the probe, and mannose as the competitively inhibiting sugar (FIG. 11B). Since the materials and procedures required when producing the array were the same as in Example 3, their description is omitted.

2. Results and Discussion

The experimental results showed a decrease in fluorescence intensity of the spots as the concentration of the competitively inhibiting sugar increased (FIG. 11), and the curve fitting of the inhibition curve was used to calculate a median inhibition concentration unique to the inhibitory substance. These results confirmed that binding with the fluorescent glycoprotein probes was due to specific binding reactions between lectins and sugar chains. In addition, it was shown that using such inhibition experiments enabled evaluation of binding strength by calculation of median inhibition concentrations, making it possible to search for binding partner molecules.

Example 5

Detection of Lectin Arrays Using Glycopeptide Probes (FIG. 12)

1. Materials and Methods
(1) Preparation of Glycopeptide Probes

After preparing Cy3-ASF according to the method described in (1) of Example 3, this Cy3-ASF was fragmented by trypsin treatment to prepare Cy3-ASF peptides.

(2) Coating of GTMS onto Slide Glasses

Coating was performed according to the method described in (2) of Example 3.

(3) Production of a Lectin Array

Lectins to be immobilized were grouped according to the major sugar recognition ability of each lectin; a total of 40 types of lectins consisting of five types of fucose-recognizing lectins, six types of sialic acid-recognizing lectins, three types of lactosamine structure-recognizing lectins, six types of galactose-recognizing lectins, 11 types of galactosamine-recognizing lectins, four types of mannose-recognizing lectins and five types of chitin structure-recognizing lectins were selected and immobilized on a slide glass to produce an array. The experimental procedure was carried out according to the method described in (3) of Example 3.

(4) Blocking of Non-Spotted Surfaces
(5) Addition of Probe Solutions and Scanning
(6) Digitization of Scanned Images The experiments for procedures (4) to (6) above were carried out by following procedures similar to the methods described in (4) to (6) of Example 3, using Cy3-ASF peptide probes.

2. Results and Discussion

As a result of the experiments, sugar chain profiles reflecting sugar chain structures were obtained by applying glycopeptide probes to the lectin array. The resulting sugar chain profiles were equivalent to those of ASF prior to enzyme digestion, and it was shown that not only glycoproteins but also the peptide digestion products of glycoproteins can be used in lectin arrays. By using this technology, the sugar chain profiles of each glycopeptide component can be observed by applying glycopeptides after fractionation by HPLC and such as probes to lectin arrays, which is useful.

Example 6

Profiling of the Sugar Chains on Glycopeptides Using a Glycopeptide Array (FIG. 13)

1. Materials and Methods
(1) Preparation of Lectin Probes

In the present example, RCA120, which strongly recognizes lactosamine structures, was used as a lectin probe, and BSA, which does not have any sugar-binding ability, was used as a negative control. Fluorescence-labeled lectin probes were prepared by fluorescent labeling using the fluorescent dye Cy3. Lectins were dissolved in a 0.1 M carbonate buffer (pH 9.3) such that the final concentration was 1 mg/mL, and then each milliliter was mixed with 1.0 mg Cy3 powder, and allowed to react in the dark for one hour while stirring occasionally. After the reaction, unreacted Cy3 dye was removed using an ultrafiltration filter kit.

(2) Coating of GTMS onto Slide Glasses

Slides were GTMS-coated according to the method described in (2) of Example 5.

(3) Production of Glycopeptide Arrays

Glycopeptides were spotted onto the GTMS-coated slide glasses prepared in (2) to produce a glycopeptide array. STAMPMAN, manufactured by Nippon Laser Electronics Ltd., was used as the microarray spotter, and spots with a diameter of approximately 0.5 mm were laid on the slide glass using a stamping pin with a tip diameter of 0.40 mm.

The immobilized glycopeptide samples used in this experiment were produced by using a lectin column to purify a glycoprotein fraction from a soluble fraction of mouse liver, fragmenting this fraction into peptides using trypsin, and then fractionating and separating the samples using HPLC. During the process of immobilizing the glycopeptides onto the slide glasses, to execute the stamping pin operating program, the conditions below were stored in the memory of a computer, which was attached to the microarray spotter. First, the stamping pin was immersed for one second in the immobilization sample solution contained in the 96-well PCR microtiter plate. It was then lifted out and contacted for one second to a predetermined location on the slide glass surface. After repeating this operation for each spot, and spotting six spots from the same sample solution in a horizontal row, the stamping pin was washed. During the washing step, the tip of the stamping pin was immersed for two seconds in a 0.05% SDS solution, the stamping pin was then dried for 15 seconds in a vacuum apparatus, then after immersion for two seconds in purified water, it was dried for 15 seconds in the vacuum apparatus. After a final immersion for two seconds in ethanol, it was dried for 15 seconds in the vacuum apparatus.

(4) Blocking of Non-Spotted Surfaces
(5) Addition of Probe Solutions and Scanning
(6) Digitization of scanned images Experiments for procedures (4) to (6) above were carried out by following the methods described in (4) to (6) of Example 3, using Cy3-RCA120 probes and Cy3-BSA probes.

2. Results and Discussion

As a result of the present experiment, it was shown that information on the structure of sugar chains attached to glycopeptides can be obtained easily and with a high throughput by arranging the glycopeptides into an array. Methods for producing glycopeptide arrays comprise 1) immobilizing purified glycopeptides, 2) immobilizing crude glycopeptides, and 3) immobilizing glycopeptide fractions separated by HPLC, etc. The experiments were able to show that arrays can be produced for each HPLC-separated fraction, and that these arrays are useful.

In the past, data on where glycopeptides were contained among fractions fractionated by HPLC was not easily obtained, because monitoring of UV absorption, fluorescence, and such was not possible. As a result of the present experiment, the use of arrays onto which various glycopeptide fractions have been immobilized has made it possible to easily determine which fractions comprise glycopeptides having what kind of sugar chain.

By using the present methods, information as to which fraction comprises a glycopeptide having a sugar chain structure which is the subject of analysis can be rapidly obtained, and thus it becomes possible to efficiently select only sugar chain-comprising fractions from a large number of fractions, and to apply this to other analyses such as mass spectroscopy, and such. In addition, when there is no information on the sugar chain structure of the glycopeptide which is the subject of analysis, or when there is no data as to what kind of lectin binds thereto, a lectin array can be used to analyze glycoproteins prior to trypsin digestion, and lectins that bind to said glycoprotein can be narrowed down from dozens of lectin types. Obtaining such data simplifies conventional procedures such as lectin blotting, which were carried out in a round-robin manner using large numbers of lectins, and there are advantages such as considerable savings of time and labor.

Example 7

Experiment Using Crude Biosamples as Probes for Lectin Arrays (FIG. 14)

1. Materials and Methods

A lectin array is used to analyze the state of sugar chain addition of glycoproteins in the body by profiling glycoprotein mixtures, particularly mixed samples derived from the body.

A glycoprotein sample extracted and purified from mouse liver and a glycoprotein sample extracted and purified from mouse brain were labeled with Cy3 to form probes, then contacted with a lectin array onto which 40 types of lectins were immobilized, and the sugar chain profile of the entire extracted mouse glycoprotein mixture was observed.

Since the materials and procedures required when producing the array were the same as in Example 3, their description is omitted.

2. Results and Discussion

The sugar chain profiles observed for the glycoprotein probe derived from mouse brain (FIG. 14A) and the glycoprotein probe derived from mouse liver (FIG. 14B) were clearly different. Prominent differences were observed between the probes, particularly in the group of lectins that recognize sialic acid. It is known that there is little addition of sialic acid to glycoproteins in the brain, and this fact accords with the trends of the experimental results. Experiments that use a crude system in this manner can rapidly and easily obtain information on the sugar chain addition of an entire sample, and thus they are suited to the purpose of collectively comparing and analyzing differences between individuals or between pathological conditions in the sugar chain structures of blood components, organs, or such.

Next, 10 mM of lactose was added as a competitively inhibiting sugar to the brain-derived glycoprotein probe used in the previous experiment, and the sugar chain profile was observed (FIG. 14C). As a result, a change was observed in the fluorescence signal pattern due to competitive inhibition, and a reduction was observed mainly in the signals of lactosamine-recognizing lectins. As shown by this experiment, even when using a lectin array for the sugar chain profiling of cruder samples, comparisons and analyses between individuals can be made easier and faster by the combined use of addition experiments that use various inhibiting sugars, and comparison and analysis after narrowing down the obtained data.

INDUSTRIAL APPLICABILITY

The present invention for the first time practically applied methods for observing interactions between lectins and sugar chains in solution and at equilibrium. This technology enables data on intermediate portions to be obtained, specifically, data on binding strength can be obtained from brightness values (for example, from 0 to 6 levels), and not the presence or absence of interaction (0 or 1) as in conventional lectin blots. This means that for "n" types of lectin-sugar chain interaction, the amount of data, which conventionally was $2^n$ sets, is increased significantly to $6^n$ sets. This technology is further expected to significantly contribute to the development of sugar chain structural analyses and various other related sugar chain engineering fields thanks to future increases in density and purity. Moreover, by producing arrays for analyzing the interactions between lectins and sugar chains for various applications, the application of these arrays can be expected in diagnosis and evaluation from stock solutions or diluted solutions of blood, body fluids, tissue extracts, and so on, as well as application to the quality control and such of glycoprotein products.

The invention claimed is:

1. A method for analyzing an interaction between a sugar chain and a protein that interacts with a sugar chain, wherein the method comprises the steps of:
    (a) contacting a fluorescently labeled subject sugar chain or subject glycoconjugate with a glass substrate onto which a protein that interacts with a sugar chain has been immobilized, wherein the glass substrate is coated with a compound comprising an epoxy group as an active group, and wherein a number of reaction vessels are formed on the glass substrate by affixing a rubber having a number of holes on the glass substrate;
    (b) measuring the intensity of an excited fluorescence after applying an evanescent wave generated by injecting an excitation light from the edge of the glass substrate, without washing the glass substrate;
    (c) digitizing the fluorescence intensity; and
    (d) quantifying the fluorescence intensity.

2. The method of claim 1, wherein the compound comprising an epoxy group as an active group is 3-glycidoxypropyl trimethoxysilane (GTMS).

3. The method of claim 1, wherein the protein that interacts with a sugar chain is a lectin, an enzymatic protein comprising a sugar-binding domain, a cytokine having an affinity for a sugar chain, or an antibody that interacts with a sugar chain.

4. The method of claim 1, wherein the glycoconjugate is a glycoprotein, a proteoglycan, or a glycolipid.

5. A glass substrate coated with a compound comprising an epoxy group as an active group, onto which a protein that interacts with a sugar chain has been immobilized, and in which a number of reaction vessels have been formed by affixing a rubber having a number of holes onto the glass.

6. The substrate of claim 5, wherein the compound comprising an epoxy group as an active group is 3-glycidoxypropyl trimethoxysilane (GTMS).

7. The substrate of claim 5, wherein the protein that interacts with a sugar chain is a lectin, an enzymatic protein comprising a sugar-binding domain, a cytokine having an affinity for a sugar chain, or an antibody that interacts with a sugar chain.

8. The method of claim 3, wherein the protein that interacts with a sugar chain is a lectin.

9. The method of claim 1, wherein the evanescent wave is generated by total internal reflection of the excitation light.

10. The method of claim 1, further comprising:
   comparing the fluorescence intensity with a database of fluorescence intensities of known sugar chains; and
   determining the identity of the labeled sugar chain by selecting a sugar chain of known structure having a matching pattern of fluorescence intensity.

11. A method for analyzing an interaction between a sugar chain and a protein that interacts with a sugar chain, comprising:
   contacting a sample comprising at least one fluorescently labeled glycoprotein with a glass slide comprising one or more lectin conjugated to the glass slide through an epoxy group of 3-glycidoxypropyl trimethoxysilane;
   applying an excitation light to the substrate from the edge of the glass substrate without washing the glass substrate;
   generating an evanescent wave by total internal reflection of the excitation light; and
   measuring intensity of emitted fluorescent light generated by the evanescent wave, wherein an increase in the emitted fluorescent light indicates the interaction between the fluorescently labeled glycoprotein and the lectin.

12. The method of claim 11, wherein the rubber is a black silicon rubber.

13. The glass substrate of claim 5, wherein the rubber is a black silicon rubber.

* * * * *